US012195800B2

(12) United States Patent
Muir et al.

(10) Patent No.: US 12,195,800 B2
(45) Date of Patent: Jan. 14, 2025

(54) METHOD TO PREDICT HERITABLE CANINE NON-CONTACT CRUCIATE LIGAMENT RUPTURE

(71) Applicant: Wisconsin Alumni Research Foundation, Madison, WI (US)

(72) Inventors: Peter Muir, Madison, WI (US); Lauren Baker, Madison, WI (US); Mehdi Momen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1076 days.

(21) Appl. No.: 17/112,608

(22) Filed: Dec. 4, 2020

(65) Prior Publication Data

US 2021/0095346 A1 Apr. 1, 2021

Related U.S. Application Data

(63) Continuation-in-part of application No. 16/194,659, filed on Nov. 19, 2018, now Pat. No. 10,858,708, which is a continuation of application No. 15/010,491, filed on Jan. 29, 2016, now Pat. No. 10,131,950.

(60) Provisional application No. 62/109,336, filed on Jan. 29, 2015.

(51) Int. Cl.
 *C12Q 1/68* (2018.01)
 *C07H 21/04* (2006.01)
 *C12Q 1/6883* (2018.01)
 *A01K 67/02* (2006.01)

(52) U.S. Cl.
 CPC ............ *C12Q 1/6883* (2013.01); *A01K 67/02* (2013.01); *C12Q 2600/118* (2013.01); *C12Q 2600/124* (2013.01); *C12Q 2600/156* (2013.01); *C12Q 2600/16* (2013.01); *C12Q 2600/172* (2013.01)

(58) Field of Classification Search
 None
 See application file for complete search history.

(56) References Cited

U.S. PATENT DOCUMENTS

| 7,510,841 | B2 | 3/2009 | Stuelpnagel et al. | |
| 10,131,950 | B2 * | 11/2018 | Muir | C12Q 1/6883 |
| 10,858,708 | B2 * | 12/2020 | Muir | C12Q 1/6883 |

OTHER PUBLICATIONS

Baker et al. (PLOS One, "Genome-wide association analysis in dogs implicates 99 loci as risk variants for anterior cruciate ligament rupture" Apr. 5, 2017, pp. 1-19). (Year: 2017).*

Alentorn-Geli et al. (2009). Prevention of non-contact anterioro curicate ligament injuries in soccer players. Part 1: Mechanisms of injury and underlying risk factors. *Knee Surgery, Sports, Traumatology, Arthroscopy*. 17:705-729.

Awano et al., (2009), Genome-wide association analysis reveals a SOD1 mutation in canine degenerative myelopathy that resembles amyotrophic lateral sclerosis, PNAS, vol. 106, No. 8, pp. 2794-2799.

Baird et al. (2014). Genome-wide association study identifies genomic regions of association for cruciate ligament rupture in Newfoundland dogs. *Animal Genetics*. 45, 4: 542-549.

Baird et al.(2014) Genetic basis of canine cruciate ligament rupture (CCLR) in dogs, *Connect Tissue Res.*, Early Online 1-7.

Baird et al. (2014) Chromosome 27:37,126,545-37,196,999—Region in detail—Canis Lupus Familiaris http://www.ensembl.org/Canis_familiaris/Location/View?db+core:+27:37126545-37196 . . . .

Beynnon et al. (2006) The relationship between menstrual cycle phase and anterior cruciate ligament injury. *Am J Sports Med.*, 34: 757-764.

Bleedorn et al. (2011). Synovitis in dogs with stable stifle joints and incipient cranial cruciate ligament rupture: A cross-sectional study. *Veterinary Surgery*. 40: 531-543.

Chang et al. (2015) Second-generation PLINK: rising to the challenge of larger and richer datasets. *GigaScience*. 4:7.

Chen et al. (2011) A genetic risk score combining ten psoriasis risk loci improves disease prediction. *PLoS One*. 6: e19454.

Chuang et al. (2014), Radiographic risk factors for contralateral rupture in dogs with unilateral cranial cruciate ligament rupture in dogs with unilateral cranial cruciate ligament rupture, PLOS ONE, 9:9:e106389, 1-10.

Clements et al. (2010), A Candidate Gene Study of Canine Joint Diseases, *The Am. Genetic Assoc..*, vol. 101, No. 1, 54-60.

Clements et al. (2011). Risk of canine cranial cruciate ligament rupture is not associated with the major histocompatibility complex. *Veterinary and Comparative Orthopaedics and Traumatology*. 1-3.

DPPA3, *Gene Cards*, Human Gene Database (2017).

Flynn et al. (2005). The familial predisposition toward tearing the anterior cruciate ligament. *The American Journal of Sports Medicine*. 33: 23-28.

Ghosh et al. (2008) Estimating odds ratios in genome scans: An approximate conditional likelihood approach. *Am J Human Genet*. 82: 1064-1074.

Girling et al. (2006). Use of biochemical markers of osteoarthritis to investigate the potential disease-modifying effect of tibial plateau levelling osteotomy. *Journal of Small Animal Practice*. 47: 708-714.

Hayashi et al. (2004). Cranial cruciate ligament pathophysiology in dogs with cruciate disease: A review. *Journal of the American Animal Hospital Association*. 40: 385-390.

Hewett et al. (2007) Effects of the menstrual cycle on anterior cruciate ligament injury risk. *Am J Sports Med*. 35: 659-668. [33,34].

(Continued)

*Primary Examiner* — Jeanine A Goldberg
(74) *Attorney, Agent, or Firm* — Joseph T. Leone; DeWitt LLP

(57) ABSTRACT

Method and kits for diagnosing propensity to non-contact cranial cruciate ligament rupture (CCLR) in a dog are described. The method includes isolating genomic DNA from a dog and then analyzing the genomic DNA from step for a single nucleotide polymorphism occurring in selected loci that have been determined to be associated with the CCLR phenotype via a genome-wide association study.

10 Claims, 8 Drawing Sheets

Specification includes a Sequence Listing.

(56) References Cited

OTHER PUBLICATIONS

Hoffman et al. (2013) A unified framework for penalized multiple regression analysis of GWAS data. PLoS Comput Biol. 9: e1003101.
Huang et al. (2009) Systematic and integrative analysis of large gene lists using DAVID bioinformatics resources. *Nat Protoc*. 4: 44-57.
Huang Q. (2015) Genetic study of complex diseases in the post-GWAS era. *J Genet Genomics*. 42: 87-98.
Illlumina (2010) Canine HD Bead Chip, 170K Chip, DataSheet: DNA Genotyping, 2010.
Karlsson et al. (2008). Leader of the pack: gene mapping in dogs and other model organisms. *Nature Reviews Genetics*. 9: 713-725.
Karlsson et al. (2013) Genome-wide analyses implicate 33 loci in heritable dog osteosarcoma, including regulatory variants near CDKN2A/B. *Genome Biol*. 14: R132.
Kendrew et al. (eds.), "The Encyclopedia of Molecular Biology," published by Blackwell Science Ltd., 1994 (ISBN 0-632-02182-9) (Book—Table of Contents Only Provided).
Khoschnau et al. (2008). Type I collagen alphal sp1 polymorphism and the risk of cruciate ligament ruptures or shoulder dislocations. *The American Journal of Sports Medicine*. 36: 2432-2436.
Kim et al. (2011) Radiographic quantitative assessment of cranial tibial subluxation before and after tibial plateau leveling osteotomy in dogs. *Am J Vet Res*. 72: 420-416.
Lee et al. (2012) INRICH: interval-based enrichment analysis for genome-wide association studies. Bioinformatics. 28: 1797-1799.
Benjamin Lewin, "Genes V," published by Oxford University Press, 1994 (ISBN 0-19-854287-9) (Book—Table of Contentsonly Provided).
Lindblad-Toh et al. (2005) Genome sequence, comparative analysis, and haplotype structure of the domestic dog. *Nature*. 438: 803-819.
Mannion et al. (2014) Genes encoding proteoglycans are associated with risk of anterior cruciate ligament ruptures. *Br J Sports Med*. 48: 1640-1646.
Muir P. (1997) Physical examination of lame dogs. *Comp Cont Ed Pract. Vet* 19: 1149-1161.
Muir et al. (2011) Contralateral cruciate survival in dogs with unilateral non-contact cranial cruciate ligament rupture. *PLoS ONE*. 6(10): e25331.
Nielen et al. (2001) Heritability estimations for diseases, coat color, body weight, and height in a birth cohort of Boxers. *Am J Vet Res*. 62: 1198-1206.
Obeidat et al. (2014) TIMAP promotes angiogenesis by suppressing PTEN-mediated Akt inhibition in human glomerular endothelial cells. *Am J Physiol Renal Physiol*. 307: F623-F633.
Ostrander et al. (2005). The canine genome. *Genome Research*. 15: 1706-1716.
Park et al. (2010) Estimation of effect size distribution from genome-wide association studies and implications for future discoveries. *Nat Genet*. 42: 570-575.
Pérez et al. (2014) Genome-wide regression and prediction with the BGLR statistical package. *Genetics*. 198: 483-495.
Plaas et al. (2011) Biochemical identification and immunolocalization of aggrecan, ADAMTS5 and inter-alpha-tryspin-inhibitor in equine degenerative suspensory ligament desmitis. *J Orthop Res*. 29: 900-906.
Posthumus et al. (2009) Genetic risk factors for anterior cruciate ligament ruptures: COL1A1 gene variant. *British Journal of Sports Medicine*. 43: 352-356.
Rahim et al. (2014) The association of genes involved in the angiogenesis-associated signaling pathway with risk of anterior cruciate ligament rupture. *J Orthop Res*. 32: 1612-1618.
Reif et al. (2003) Comparison of tibial plateau angles in normal and cranial cruciate deficient stifles of Labrador retrievers. *Vet Surg*. 32: 385-389.
Safra et al. (2011) Expanded dog leukocyte antigen (DLA) single nucleotide polymorphism (SNP) genotyping reveals spurious class II associations, *Veterinary Journal*, col. 189, 220-226.
Schierding et al. (2014) The missing story behind genome wide association studies: single nucleotide polymorphisms in gene deserts have a story to tell. *Front Genet*. 5: 39.
Schumann R. (2011) Old and new findings on lipopolysaccharide-binding protein: a soluble pattern-recognition molecule. *Biochem Soc Trans*. 39: 989-993.
Sutton et al. (2013) Anterior cruciate ligament rupture: Differences between males and females. *J Am Acad Orthop Surg*. 21: 41-50.
Svishcheva et al. (2012) "Rapid variance components-based method for whole-genome association analysis," *Nature Genetics* 44:1166-1170.
Tacher et al. (2005) Olfactory Receptor Sequence Polymorphism within and between Breeds of Dogs, *J. of Heredity*, vol. 96, No. 7, 812-826.
Tang et al. (2014) Candidate genes and functional noncoding variants identified in a canine model of obsessive-compulsive disorder. *Genome Biol*. 15: R25.
Tiira et al. (2012) Environmental Effects on compulsive Tail Chasing in Dogs, *PLos ONE*, vol. 7, No. 7, ef1684.
Waggett et al (2006) Connexin 32 and 43 gap junctions differentially modulate tenocyte response to cyclic mechanical load. Eur J Cell Biol. 85: 1145-1154.
Whitehair et al (1993). Epidemiology of cranial cruciate ligament rupture in dogs. *Journal of the American Veterinary Medical Association*. 203: 1016-1019.
Wilke et al (2005). Estimate of the annual economic impact of treatment of cranial cruciate ligament in jury in dogs in the United States. *Journal of the American Veterinary Medical Association*. 227(10): 1604-7.
Wilke et al (2008) Inheritance of rupture of cranial cruciate ligament in Newfoundlands. *J Am Vet Med Assoc*. 228: 61-64.
Wilke et al. (2009). Identification of chromosomal regions associated with cranial cruciate ligament rupture in a population of Newfoundlands. *American Journal of Veterinary Research*. vol. 70,8: 1013-1017.
Witsberger et al. (2008). Prevalence of and risk factors for hip dysplasia and cranial cruciate ligament deficiency in dogs. *Journal of the American Veterinary Medical Association*. 232 (12): 1818-1824.
Yang et al. (2011) GCTA: a tool for Genome-wide Complex Trait Analysis. *Am J Hum Genet*. 76-82. [PubMed ID: 21167468].
Young et al. (2009) Maturational alterations in gap junction expression and associated collagen synthesis in response to tendon function. *Matrix Biol* 2009;28: 311-323.
Zhang CH. (2010)Nearly unbiased variable selection under minimax concave penalty. *Ann Stat*. 38: 894-942.
Zhou et al. (2013) Polygenic modeling with Bayesian sparse linear mixed models. PLoS Genetics. 9: e1003264.
Zhou et al (2012) Genome-wide efficient mixed-model analysis for association studies. *Nat Genet*. 44: 821-824.

* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Canis familiaris

<400> SEQUENCE: 1

Asp Glu Ala His
1

METHOD TO PREDICT HERITABLE CANINE NON-CONTACT CRUCIATE LIGAMENT RUPTURE

CROSS-REFERENCE TO RELATED APPLICATIONS

This is a continuation-in-part of application Ser. No. 16/194,659, filed Nov. 19, 2018, now U.S. Pat. No. 10,858,708, issued Dec. 8, 2020, which is a continuation of application Ser. No. 15/010,491, filed Jan. 29, 2016, now U.S. Pat. No. 10,131,950, issued Nov. 20, 2018, which claims priority to provisional application Ser. No. 62/109,336, filed Jan. 29, 2015, which is incorporated herein by reference.

BACKGROUND

The domestication of the dog and subsequent development of many dog breeds has been declared one of the greatest genetic experiments ever conducted by human beings. (Ostrander, E. A., Wayne, R. K. (2005).) The canine genome. *Genome Research.* 15: 17061716. There are now over 300 unique breeds of dog. These breeds have been purposefully developed with specific behavioral and physical traits in mind, thereby showcasing the incredible genetic diversity of the species—from Great Danes to Chihuahuas. However, an unintended consequence of breed development is an increased incidence of disease states within certain breed. Many of the same disease states seen in certain dog breeds are also seen in human beings. Notably, the reduced genetic diversity in purebred dogs has generated stretches of linkage disequilibrium (LD) that are 40 to 100 times longer in dogs than in humans. Karlsson, E. K., Lindblad-Toh, K. (2008). Leader of the pack: gene mapping in dogs and other model organisms. *Nature Reviews Genetics.* 9: 713-725. This presents a unique opportunity to study the genetic predisposition to disease more efficiently by first identifying associations in dogs and using that knowledge to inform human medical research.

Cruciate ligament rupture is one condition that occurs frequently in both dogs and humans. The cranial cruciate ligament (CCL) is one of two intra-articular ligaments in the canine stifle (knee) joint, the other being the caudal cruciate ligament. The CCL is analogous to the human anterior cruciate ligament (ACL), both anatomically and functionally. Both canine populations and human populations experience a condition where the CCL/ACL ruptures without a traumatic force. This is known as non-contact cruciate ligament rupture. See Alentorn-Geli, E., Myer, G. D., Silvers, H. J., Samitier, G., Romero, D., Lazaro-Haro, C., Cugat, R. (2009). Prevention of non-contact anterioro curicate ligament injuries in soccer players. Part 1: Mechanisms of injury and underlying risk factors. Knee Surgery, Sports, Traumatology, Arthroscopy. 17:705-729. Canine non-contact cranial cruciate ligament rupture (CCLR) is the most common cause of pelvic limb lameness in dogs. CCLR is diagnosed in approximately 20% of canine cases seen for lameness at university institutions. Wilke, V. L., Robinson, D. A., Evans, R. B., Rothschild, M. F., Conzemius, M. G. (2005). Estimate of the annual economic impact of treatment of cranial cruciate ligament injury in dogs in the United States. *Journal of the American Veterinary Medical Association.* 227(10): 1604-7. The canine condition is characterized by progressive stifle joint synovitis and osteoarthritis that leads to gradual fraying and eventual mid-substance rupture of the cranial cruciate ligament. Instability of the stifle joint as a result of CCLR is often debilitating and requires surgical treatment. The cost of surgery and pain management has a large economic impact. It has been estimated that American pet owners alone spend more than $1 billion per year on CCLR management (Wilkie et al., supra). When a dog presents with one stable and one unstable stifle, evidence of disease can often be found in the stable joint. (Bleedorn, J. A., Greuel, E. N., Manley, P. A, Schaefer, S. L., Markel, M. D., Holzman, G., Muir, P. (2011). Synovitis in dogs with stable stifle joints and incipient cranial cruciate ligament rupture: A cross-sectional study. *Veterinary Surgery.* 40: 531-543.) More than 50% of dogs with unilateral CCLR will ultimately go on to rupture the contra-lateral ligament. (Muir, P., Schwartz, Z., Malek, S., Kreines, A., Cabrera, S. Y., Buote, N. J., Bleedorn, J. A., Schaefer, S. L., Holzman, G., Hao, Z. (2011) Contralateral cruciate survival in dogs with unilateral non-contact cranial cruciate ligament rupture. *PLoS ONE.* 6(10): e25331.) While surgical stabilization does lead to clinical improvement, it does not cure the underlying mechanism that led to ligament degeneration. Thus even with surgical intervention osteoarthritis will continue to develop in the joint over time. (Girling, S. L., Bell, S. C., Whitelock, R. G., Rayward, R. M., Thomson, D. G., Carter, S. C., Vaughan-Thomas, A., Innes, J. F. (2006). Use of biochemical markers of osteoarthritis to investigate the potential disease-modifying effect of tibial plateau levelling osteotomy. *Journal of Small Animal Practice.* 47: 708-714.)

While several hypotheses have been investigated, the mechanism underlying the cruciate rupture condition in dogs and humans remains unclear. Risk factors for disease initiation and disease progression in dogs have been investigated. Neutering, weight, and gender have all been investigated as risk factors for disease initiation. However, the most important risk factor for disease initiation in dogs is breed. The prevalence of CCLR in the Newfoundland, Labrador Retriever, and Boxer has been estimated at 8.9%, 5.79%, and 5.24% respectively. In contrast, other breeds, such as the Greyhound and Old English Sheepdog, experience much lower prevalence of CCLR (0.5% and 0.97%, respectively). The Labrador Retriever breed has greater stifle joint laxity and a weaker CCL as compared to the Greyhound. Family-based pedigree studies indicate that heritability of CCLR is high for a complex trait. Data reveal a heritability estimate of 0.27 in the Newfoundland and 0.28 in the Boxer. Human medical research has also begun to look into genetics as a potential risk factor for ACL rupture. Individuals with a blood relative who has ruptured their ACL are at two-times (2×) greater risk of rupturing their own. Recent research in humans suggests that a rare COL1A1 gene variant may be protective against ACL rupture in young athletes. See Clements, D. N., Kennedy, L. J., Short, A. D. Barnes, A., Ferguson, J., Ollier, W. E. R. (2011). Risk of canine cranial curicate ligament rupture is not associated with the major histocompatibility complex. Veterinary and Comparative Orthopaedics and Traumatology. 1-3; Hayashi, Kei., Manley, P. A., Muir, P. (2004). Cranial cruciate ligament pathophysiology in dogs with cruciate disease: A review. Journal of the American Animal Hospital Association. 40: 385-390; Witsberger, T., Villamil, J., Schultz, L., Hahn, A., Cook, J. (2008). Prevalence of and risk factors for hip dysplasia and cranial cruciate ligament deficiency in dogs. Journal of the American Veterinary Medical Association. 232 (12): 1818-1824; Whitehair, J. G., Vasseur, P. B., Willits, N. H. (1993). Epidemiology of cranial cruciate ligament rupture in dogs. Journal of the American Veterinary Medical Association. 203: 1016-1019; Wilke, V. L., Conzemius, M. G., Kinghorn, B. P., Macrossan, P. E., Cai, W., Rothschild, M. F. (2006).

Inheritance of rupture of cranial cruciate ligament in Newfoundlands. Journal of the American Veterinary Medical Association. 228: 61-64; Nielen, A. L., Janss, L. L., Knol, B. W. (2001). Heritability estimations for diseases, coat color, body weight, and height in a birth cohort of Boxers. American Journal of Veterinary Research. 62, 8: 1198-1206; Flynn, R. K., Pedersen, C. L., Birmingham, T. B., Kirkley, A., Jackowski, D., Fowler, P. J. (2005). The familial predisposition toward tearing the anterior cruciate ligament. The American Journal of Sports Medicine. 33: 23-28; Posthumus, M., September, A. V., Keegan, M., O'Cuinneagain, D., Van der Merwe, W., Schwellnus, M. P., Collins, M. (2009) Genetic risk factors for anterior cruciate ligament ruptures: COL1A1 gene variant. British Journal of Sports Medicine. 43: 352-356; and Khoschnau, S., Melhus, H., Jacobson, A., Rahme, H., Bengtsson, H., Ribom, E., Grundberg, E., Mallmin, H., Michaelsson, K. (2008). Type I collagen alpha1 sp1 polymorphism and the risk of cruciate ligament ruptures or shoulder dislocations. The American Journal of Sports Medicine. 36: 2432-2436.

Two studies have mapped the CCLR trait to the canine genome. Associations with CCLR were reported on canine chromosomes 3, 5, and 15 using a broad genomic scan of 495 microsatellite markers in Newfoundland dogs. (Wilke, V. L., Zhang, S., Evans, R. B., Conzemius, M. G., Rothschild, M. F. (2009). Identification of chromosomal regions associated with cranial cruciate ligament rupture in a population of Newfoundlands. *American Journal of Veterinary Research*. Vol. 70, 8: 1013-1017.) More recently, a high-resolution genome-wide association study (GWAS) for CCLR, also in the Newfoundland breed, found single nucleotide polymorphism (SNP) associations on canine chromosomes 1, 3, 10, 12, 22, and 33. (Baird, A. E. G., Carter, S. D., Innes, J. F., Ollier, W., Short, A. (2014). Genome-wide association study identifies genomic regions of association for cruciate ligament rupture in Newfoundland dogs. *Animal Genetics*. 45, 4: 542-549.) The 65 most significant SNPs were re-genotyped with a custom chip array, which identified significant regions on chromosomes 1, 3, and 33. These regions contained several genes that are highly expressed in the nervous system, suggesting a potential neuronal signaling component to CCLR risk. The Baird et al. GWAS was unable to replicate results from the earlier Wilkie et al. microsatellite marker study.

SUMMARY OF THE INVENTION

To advance understanding of the genetic risk factors contributing to CCLR, a GWAS was performed to identify candidate genomic regions associated with the CCLR trait. To take advantage of the long-range LD present in dogs, the GWAS was limited to a single high-risk breed, the Labrador retriever, which has a high prevalence of CCLR. The Labrador retriever is also the most common breed in the United States according to records of the American Kennel Club.

As disclosed herein, CCLR is associated with multiple regions of the canine genome. Thus, by analyzing dogs for mutations in these CCLR-associated regions, the propensity of their progeny to carry the trait, and thus to experience CCLR, can be determined. This information can then be used to guide breeding efforts to reduce the occurrence of CCLR.

Thus, disclosed herein is a method for diagnosing propensity to non-contact cranial cruciate ligament rupture (CCLR) in a dog. The method comprises isolating genomic DNA from a dog and then analyzing the genomic DNA for single nucleotide polymorphisms occurring within, or in a genomic interval of about 2 Mb upstream or downstream of, at least one locus revealed herein to be associated with the CCLR phenotype. These loci include BICF2P1126668, BICF2P260555, BICF2P599385, BICF2P1465216, BICF2S23135243, BICF2P170661, TIGRP2P78405, BICF2P890246, BICF2P401973, BICF2G630114782, BICF2G630815470, BICF2G630815474, BICF2S23448539, BICF2P1121006, BICF2G630371956, BICF2S2356299, BICF2P526639, BICF2P154295, BICF2P412007, BICF2S23645462, BICF2G630373050, and BICF2P471347. The dog has an increased propensity for CCLR when five or more SNPs (or 10 or more, or 15 or more, or 20 or more) are detected in the dog's genomic DNA.

Also disclosed herein is a method for diagnosing propensity to non-contact cranial cruciate ligament rupture (CCLR) in a dog. Here, the method focuses on mutations in specific genes. The method comprises isolating genomic DNA from a dog. The DNA is then analyzed for single nucleotide polymorphisms occurring within, or in a genomic interval of about 2 Mb upstream or downstream of, at least one gene selected from the group consisting of CDH18, DPPA3, UBE2D1, ASS1, SPRED2, DLC1, DYSF, SCGB2, CHST2, SLC15A, ANO2, ERRFI1, SCGB2, and TRIM42. Again, the dog has an increased propensity for CCLR when five or more SNPs (or 10 or more, or 15 or more, or 20 or more) are detected in the dog's genomic DNA.

Also disclosed herein are kits for diagnosing the propensity to non-contact cranial cruciate ligament rupture (CCLR) in a dog. The kits comprise oligonucleotide probes or primers dimensioned and configured to bind selectively to single nucleotide polymorphism occurring within, or in a genomic interval of about 2 Mb upstream or downstream of at least one locus selected from the group consisting of BICF2P1126668, BICF2P260555, BICF2P599385, BICF2P1465216, BICF2S23135243, BICF2P170661, TIGRP2P78405, BICF2P890246, BICF2P401973, BICF2G630114782, BICF2G630815470, BICF2G630815474, BICF2S23448539, BICF2P1121006, BICF2G630371956, BICF2S2356299, BICF2P526639, BICF2P154295, BICF2P412007, BICF2S23645462, BICF2G630373050, and BICF2P471347. Instructions for use of the kit are typically included.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. Unless otherwise stated, the indefinite articles "a" and "an" mean "one or more." When referring to a previously stated element, the definite article "the" does not limit the stated definition of "a" and "an," as being "one or more." All combinations of method or process steps as used herein can be performed in any order, unless otherwise specified or clearly implied to the contrary by the context in which the referenced combination is made.

The methods and kits disclosed herein can comprise, consist of, or consist essentially of the essential elements and limitations described herein, as well as any additional or optional steps, ingredients, components, or limitations described herein or otherwise useful in gathering, preparing, and sequencing genomic DNA for analysis.

BRIEF DESCRIPTION OF THE DRAWINGS

FIG. 4 is a graph showing the distribution of the number of ACL rupture risk loci in case and control groups of Labrador Retriever dogs. The number of risk alleles in cases and controls is significantly different (P<2.2E−16).

FIG. 5 is a graph depicting ACL rupture odds ratios of weighted genetic risk scores (wGRS) relative to the first quartile. Vertical bars represent the 95% confidence intervals. * Odds ratio is significantly different from the reference first quartile.

DETAILED DESCRIPTION

Abbreviations and Definitions

Figure 1:
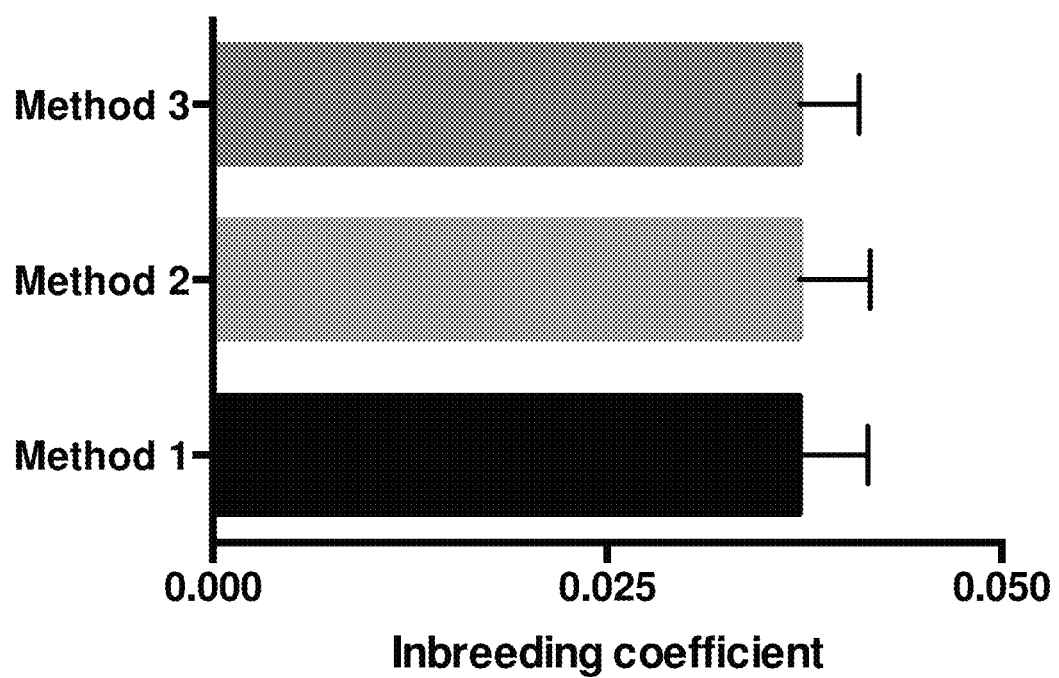
FIG. 1 is a graph showing that the Labrador Retriever is a dog breed with a relatively low amount of inbreeding. Whiskers represent the minimum and maximum values for each analysis method (n=237 dogs).

CCLR: cranial cruciate ligament rupture (non-contact).
EDTA: Ethylenediaminetetraacetic acid.
GEMMA: Genome-wide efficient mixed model association.
GenABEL is an online project is to provide a free framework for collaborative, robust, transparent, and open source-based development of statistical genomics methodology. See http://www.genabel.org/.

GRAMMAR-Gamma is a genomic analysis program which is available through GenABEL. See also Svishcheva, G. R., Axenovich, T. I., Belonogova, N. M., van Duijn, C. M., and Aulchenko, Y. S. (2012) "Rapid variance components-based method for whole-genome association analysis," Nature Genetics 44:1166-1170.

GWAS: Genome-wide association study. A genome-wide association study is an analysis of genetic variation at specified loci in different individuals to see if any variant(s) is (are) associated with a phenotypic trait. As the name indicates, genetic markers across the complete genome of each individual test subject are tested to find genetic variations associated with a particular disease, in this case CCLR in dogs. Once new genetic associations are identified, the information is used to detect, treat and/or prevent the disease. Such studies are particularly useful in finding genetic variations that contribute to common, but complex diseases.

LD: Linkage disequilibrium. Linkage disequilibrium is the non-random association of alleles at two or more loci that descend from single, ancestral chromosomes.

MDS: multidimensional scaling.

MLM, LLM (synonymous): mixed linear model, linear mixed model, respectively.

P3D: Population parameters previously determined.

PLINK: PLINK is a free, open-source whole genome association analysis program that performs a range of large-scale genomic analyses in a computationally efficient manner. The PLINK software was developed (and continues to be refined) by Shaun Purcell and others at the Center for Human Genetic Research, Massachusetts General Hospital, and the Broad Institute of Harvard & MIT. PLINK v.1.9 is available online as of May 15, 2014 at http://pngu.mgh.harvard.edu/~purcell/plink/.

SNP: Single nucleotide polymorphism.

TASSEL: Trait analysis by association, evolution and linkage.

Unless otherwise noted, technical terms are used according to conventional usage. Definitions of common terms in genetics, genomics, and molecular biology may be found in Benjamin Lewin, "Genes V," published by Oxford University Press, 1994 (ISBN 0-19-854287-9) and Kendrew et al. (eds.), "The Encyclopedia of Molecular Biology," published by Blackwell Science Ltd., 1994 (ISBN 0-632-02182-9).

Canine Samples and Phenotyping:

DNA was isolated from client-owned Labrador Retrievers using blood or buccal swabs. A four-generation pedigree was collected from each dog to ensure purebred status and identify siblings, which were excluded from the GWAS. Each dog underwent an orthopaedic examination that included assessment of knee stability (Muir P. Physical examination of lame dogs. Comp Cont Ed Pract. Vet 1997; 19: 1149-1161). Radiographs of the affected knee(s) were also assessed in cases. In addition, lateral weight-bearing knee radiographs (Kim S E, Lewis D D, Pozzi A, Seibert R L, Winter M D. Radiographic quantitative assessment of cranial tibial subluxation before and after tibial plateau leveling osteotomy in dogs. Am J Vet Res. 2011; 72: 420-416) were made to screen phenotype-negative control dogs. While it is not possible to identify the cruciate ligaments radiographically in the dog, compression of the infrapatellar fat pad in the knee by synovial effusion and knee osteophytosis are degenerative changes typically associated with ACL rupture (Chuang C, Ramaker M A, Kaur S, Csomos R A, Kroner K T, Bleedorn J A, et al. Radiographic risk factors for contralateral rupture in dogs with unilateral cranial cruciate ligament rupture). Dogs were considered cases if anterior translation of the tibia was detected clinically and radiographic signs were consistent with ACL rupture. Labrador Retrievers ≥8 years of age have less than a 6% chance of developing ACL rupture (Reif U, Probst C W. Comparison of tibial plateau angles in normal and cranial cruciate deficient stifles of Labrador retrievers. Vet Surg. 2003; 32: 385-389). Therefore, control dogs were ≥8 years of age with a normal orthopaedic clinical exam and normal knee radiographs. Habitual activity of each dog was documented using a questionnaire.

Genome-Wide Association:

Genome-wide SNP genotyping was performed in 98 cases and 139 controls using the Illumina CanineHD BeadChip, which genotypes 173,662 SNPs evenly spaced across the genome. Data underwent quality control filtering using PLINK (Chang C C, Chow C C, Tellier LCAM, Vattikuti S, Purcell S M, Lee J J. Second-generation PLINK: rising to the challenge of larger and richer datasets. GigaScience. 2015; 4:7). All samples had a genotyping call rate of ≥95%. 49,859 SNPs were excluded because minor allele frequency (MAF) was ≤0.05 and 7,468 SNPs were excluded because of a low genotyping rate (≤95%). 153 SNPs were excluded because of deviation from Hardy-Weinberg equilibrium at P<1E−07. 118, 992 SNPs were used for further analysis.

To account for ancestral population structure and family relatedness in the study dogs, single marker linear mixed model (LMM) analysis was performed using GCTA (Genome-wide Complex Trait Analysis) (Yang K, Lee S H, Goddard M E, Visscher. GCTA: A tool for genome-wide complex trait analysis. Am J Hum Genet. 2011; 88: 76-82) and GEMMA (Genome-wide Efficient Mixed Model Association) (Zhou X, Stephens M. Genome-wide efficient mixed-model analysis for association studies. *Nat Genet.* 2012; 44: 821-824), software tools optimized for complex trait GWAS. Penalized Unified Multiple-locus Association (PUMA), in which all SNPs are analyzed together, was also used to aid detection of weaker associations often found in complex traits (Hoffman G E, Logsdon B A, Mezey J G. PUMA: A unified framework for penalized multiple regression analysis of GWAS data. PLoS Comput Biol. 2013; 9: e1003101). We used logistic regression and a 2D-MCP penalty for this analysis (Hoffman G E, Logsdon B A, Mezey J G. PUMA: A unified framework for penalized multiple regression analysis of GWAS data. PLoS Comput Biol. 2013; 9: e1003101; Zhang C H. Nearly unbiased variable selection under minimax concave penalty. Ann Stat. 2010; 38: 894-942). In the PUMA analysis, the first 20 eigenvectors were used as covariates in the association analysis to correct for population structure. Eigenvectors were obtained by principal component analysis using GCTA. Because neutering has a significant effect on risk of ACL rupture, it was included as a covariate with the GEMMA, GCTA, and PUMA analyses.

Genome-Wide Significance:

We defined genome-wide significance using permutation testing. Use of a Bonferroni correction for the number of SNPs tested is too conservative in dog breeds, as extensive LD means that SNPs are often inherited in haplotype blocks (Lindblad-Toh K, Wade C M, Mikkelsen T S, Karlsson E K, Jaffe D B, Kamal M, et al. Genome sequence, comparative analysis, and haplotype structure of the domestic dog. Nature. 2005; 438: 803-819). We defined genome-wide significance by randomly permuting the phenotypes and re-running the GWAS LMM 1,000 times. Genome-wide significance was defined by identifying the 5% quantile of the set of minimum P-values from the GWAS permutations. Additionally, we calculated the number of haplotype blocks in the Labrador Retriever SNP data using PLINK, using LD windows of 500 kb, 1 Mb, and 5 Mb and used the number of haplotype blocks to estimate genome-wide significance by Bonferroni correction of P<0.05. To facilitate further dissection of genetic variants associated with the ACL phenotype, we also identified a larger set of candidate ACL rupture regions at P<5E−04 (Karlsson E K, Sigurdsson S, Ivansson E, Thomas R, Elvers I, Wright J, et al. Genome-wide analyses implicate 33 loci in heritable dog osteosarcoma, including regulatory variants near CDKN2A/B. Genome Biol. 2013; 14: R132). Although some of the regions included may not be true associations, this would likely weaken rather than strengthen the gene set and pathway analyses, leading to false negatives rather than false positives.

Defining Associated Loci in the Genome:

Linkage-disequilibrium (LD) clumping using PLINK was used to define regions of association with the ACL rupture trait from the GWAS results. LD clumping defined regions around SNPs associated at P<5E−04. Regions within 1 Mb of the index SNP ($r^2$>0.8 and P<0.01). We also used GCTA to explain the phenotype variance explained by the associated loci, which were defined as SNPs with $r^2$>0.2 within 5 Mb of the peak SNP in each locus (Tang R, Noh H J, Wang D, Sigurdsson S, Swofford R, Perlosko M, et al. Candidate genes and functional noncoding variants identified in a canine model of obsessive-compulsive disorder. Genome Biol. 2014; 15: R25).

For complex trait GWAS with a large number of risk loci, loci that are not discovered are expected to have smaller effect sizes in a second generation GWAS, because those with larger effect sizes will have been identified in the first round of GWAS. To estimate the number of risk loci that are likely associated with ACL rupture, we used INPower. Odds ratios were corrected for the winner's curse before INPower analysis was performed. See Park J-HM, Wacholder S, Gail M, Peters U, Jacobs K B, Chanock S J, et al. Estimation of effect size distribution from genome-wide association studies and implications for future discoveries. Nat Genet. 2010; 42: 570-575 and Ghosh A, Zou F, Wright F A. Estimating odds ratios in genome scans: An approximate conditional likelihood approach. Am J Human Genet. 2008; 82: 1064-1074.

Genetic Risk Score Computation:

Two approaches were used to calculate the genetic risk scores (GRS), a simple risk alleles count method (cGRS) and a weighted method (wGRS) (Chen H, Poon A, Yeung C, Helms C, Pons J, Bowcock A M, et al. A genetic risk score combining ten psoriasis risk loci improves disease prediction. PLoS One. 2011; 6: e19454). The wGRS weights each risk allele by the logarithm odds ratio (Log(OR)) for that allele. The wGRS is a linear combination of the number of risk alleles weighted by the Log(OR) as coefficients. The Mann-Whitney U test was used to compare cGRS scores for each LMM in case and control groups. To estimate the total risk captured by the genetic risk scoring for each LMM, we calculated the odds ratios according to the wGRS quartiles. We also measured the discriminative power attributable to the GRS by plotting receiver operating characteristic (ROC) curves and calculated the area under the curve (AUC) for the Labrador Retriever case and control dogs. AUC 95% confidence intervals were calculated using 2000 stratified bootstrap replicates. An R software package (http://www.r-project.org/) was used for these analyses.

Pathway Analysis:

Pathway analysis was performed with two methods. DAVID (Huang D W, Sherman B T, Lempicki R A. Systematic and integrative analysis of large gene lists using DAVID bioinformatics resources. Nat Protoc. 2009; 4: 44-57) analyses were run on the ACL rupture loci identified from our GWAS. ACL rupture loci were transposed to CanFam 3.1 coordinates (genome.ucsc.edu/cgi-bin/hgLiftOver) with 500 kB flanks added to the start and end and gene size correction turned on (Tang R, Noh H J, Wang D, Sigurdsson S, Swofford R, Perlosko M, et al. Candidate genes and functional noncoding variants identified in a canine model of obsessive-compulsive disorder. Genome Biol. 2014; 15: R25). A list of genes from the liftover coordinates was then analyzed. Probability values were evaluated after Benjamini correction with DAVID.

Pathway analysis with INRICH was performed on canFam2 intervals using a map file lifted over from the canFam3.1 Broad Improved Canine Annotation catalog (UCSC Genome Browser) (Lee P H, Dushlaine C O, Thomas B, Purcell S M. INRICH: interval-based enrichment analysis for genome-wide association studies. Bioinformatics. 2012; 28: 1797-1799). We used 1,000,000 permutations matched for region size, SNP density, and gene number. INRICH reports significance for each gene set and the experiment-wide significance, correcting for the number of gene sets ($P_{corr}$). We considered $P_{corr}<0.05$ to be significant. We tested gene sets from the KEGG (Kyoto Encyclopedia of Genes and Genomes), Gene Ontology, and MSigDB (Molecular Signatures Database).

Heritability Estimation:

Narrow sense heritability was estimated from SNPs using the BGLR statistical package (Pérez P, de los Campos G. Genome-wide regression and prediction with the BGLR statistical package. Genetics. 2014; 198: 483-495). SNPs with missing genotypes were filtered out using PLINK. Heritability estimation was performed using SNPs. A genomic best linear unbiased prediction (GBLUP) model was fitted using a SNP-derived genomic relationship matrix using a non-parametric reproducing kernel Hilbert spaces (RKHS) method as described in Pérez (2014). Broad sense heritability was also estimated using a data matrix prepared from pedigrees. To fit the model, 30,000 iterations of the Gibbs sampler were used with burn-in of 5,000 iterations. A correction factor was used to transform the heritability estimate on the observed scale from the regression model to the liability scale for a binary trait (Zhou X, Caronetto P, Stephens M. Polygenic modeling with Bayesian sparse linear mixed models. PLoS Genetics. 2013; 9: e1003264) and a population prevalence of 0.0579 (Witsberger T H, Villamil J A, Schultz L G, Hahn A W, Cook J L. Prevalence of and risk factors for hip dysplasia and cranial cruciate ligament deficiency in dogs. J Am Vet Med Assoc. 2008; 232: 1818-1824) was used for this correction.

Linkage Disequilibrium Analysis:

After obtaining the results from each MLM, LD-based clumping was calculated in PLINK to define associated regions in LD with the most significant SNPs ($r^2>0.5$, within 2 Mb of the associated SNP). These settings were modified from another GWAS for a complex trait in dogs. (Karlsson et al. (2013). Genome-wide analyses implicate 33 loci in heritable dog osteosarcoma, including regulatory variants near CDKN2A/B. Genome Biology. 14:R132.) These regions were then investigated with the NCBI Canine Genome Map Viewer to identify nearby genes using the CanFam 3.0 reference sequence.

GWAS Population of Labrador Retrievers:

We genotyped 237 Labrador Retrievers using the Illumina CanineHD BeadChip, removing SNPs with call rates of <95%. No dogs were removed after SNP filtering. The final dataset contained 118,992 SNPs from 98 cases and 139 phenotype-negative controls. Median inbreeding coefficient was 0.025 (FIG. 1). The ratio of females to males in the case and control groups was 0.92 and 0.83 respectively. Of the 114 females, 99 were ovariohysterectomized (0.87). Of the 123 males, 96 were castrated (0.78). Mean age of the dogs in the case and control groups was 6.0±2.5 years and 10.4±1.7 years, respectively.

Figure 2:
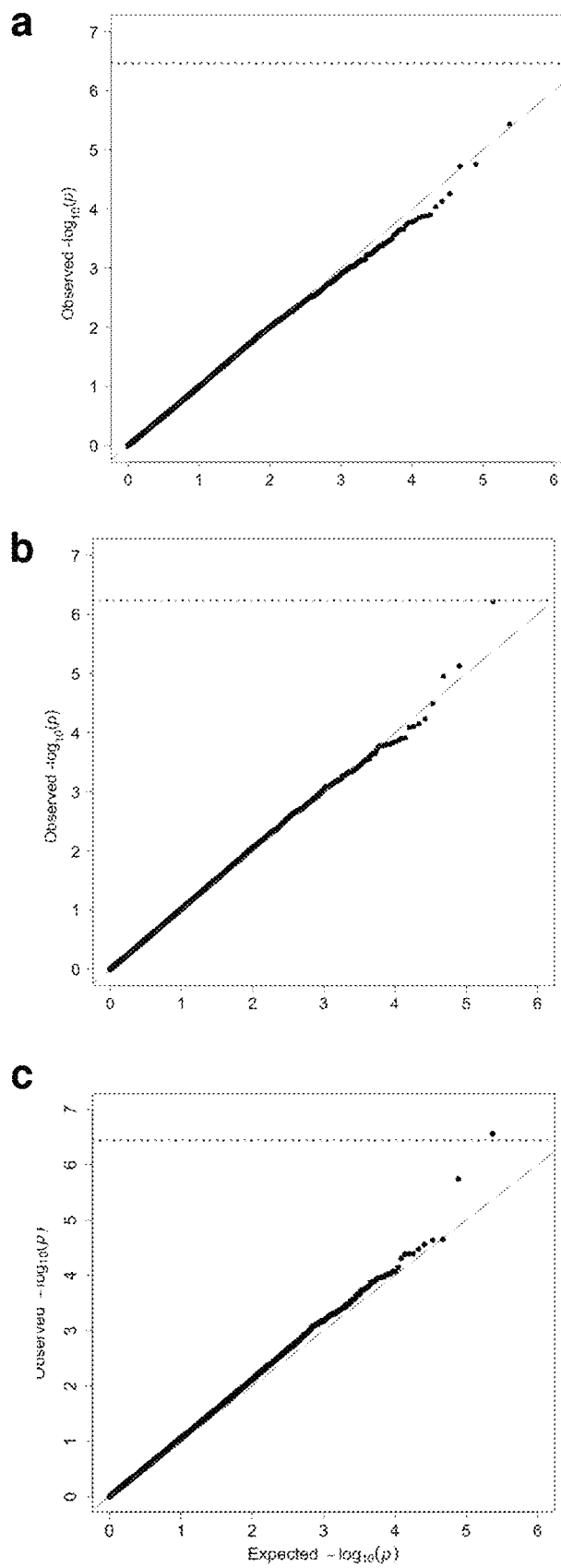
FIG. 2 is a series of graphs demonstrating that linear mixed model GWAS corrects for population structure and identifies 98 ACL associated loci explaining a large proportion of phenotypic variance. For each linear mixed model (LMM), the QQ plots show no evidence of population stratification relative to the expected distribution. Permutation testing with each model determined genome-wide significance at panel (a) P<3.63E−7 for GCTA (Genome-wide Complex Trait Analysis), λ=0.987; panel (b) P<6.097E−7 for GEMMA (Genome-wide Efficient Mixed Model Association), λ=0.994; and panel (c) P<4.01E−7 for PUMA (Penalized Unified Multiple-locus Association, λ=1.012. The plots represent analysis of 118,992 SNPs from 98 cases and 139 phenotype-negative controls. Panel (d): with GCTA, 36 loci have P<5E−4, with the most significant locus located in CFA 26, which did not meet genome-wide significance defined by minimum p-values from permutation testing. Panel (e): with GEMMA, 47 loci have P<5E−4, with the locus on CFA 26 meeting genome-wide significance defined by minimum p-values from permutation testing. Panel (f): with PUMA, 65 loci were significant at P<5E−4 and the locus on CFA 26 exceeded genome-wide significance defined by minimum p-values from permutation testing.
Figure 2:
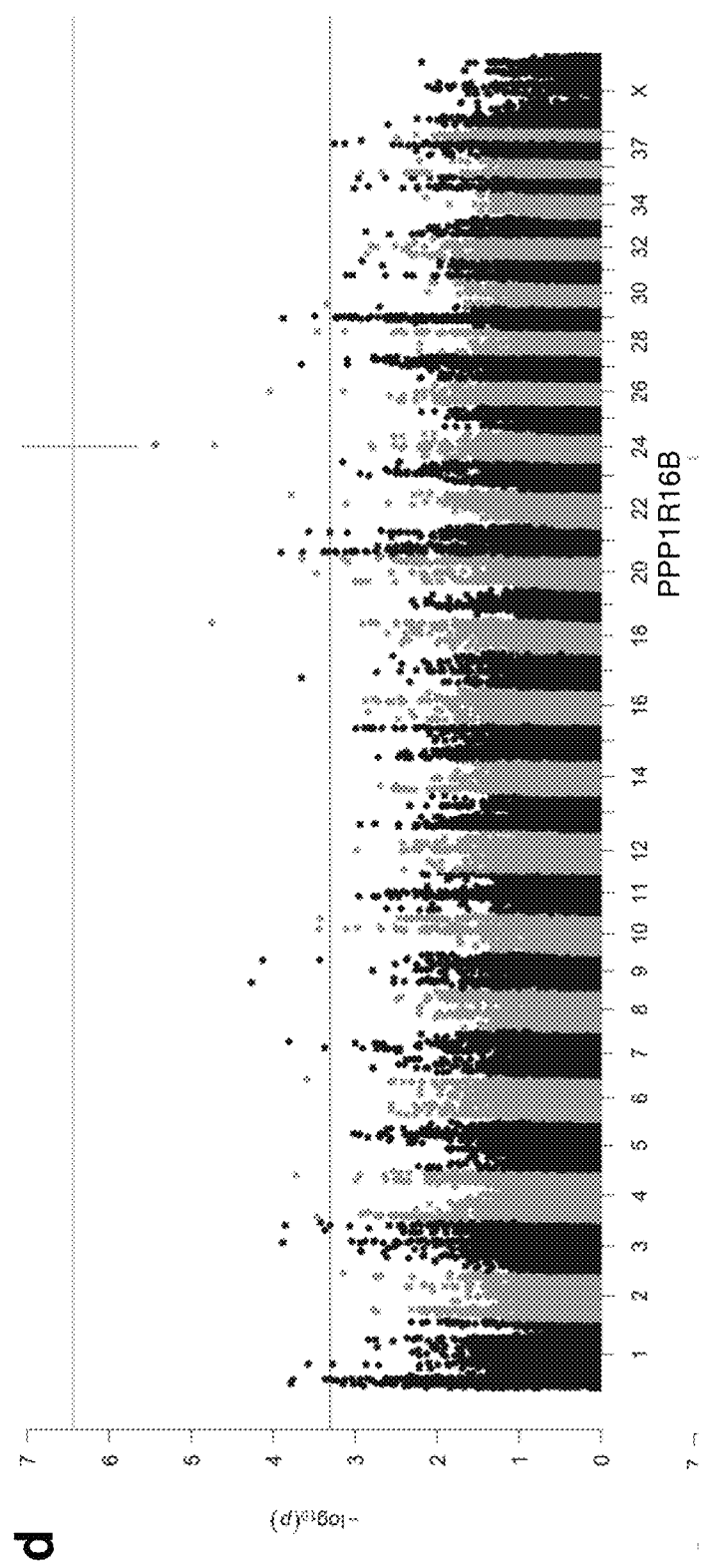
Figure 2:
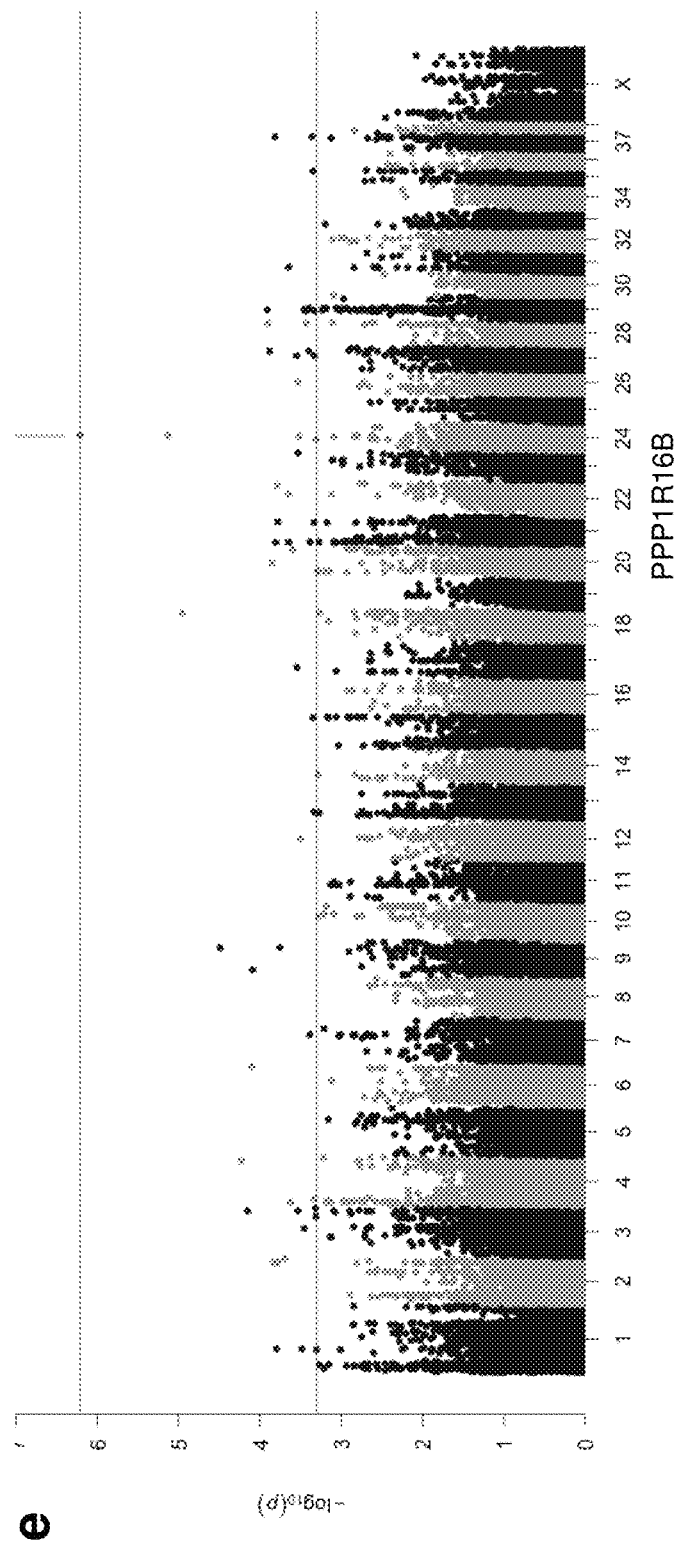
Figure 2:
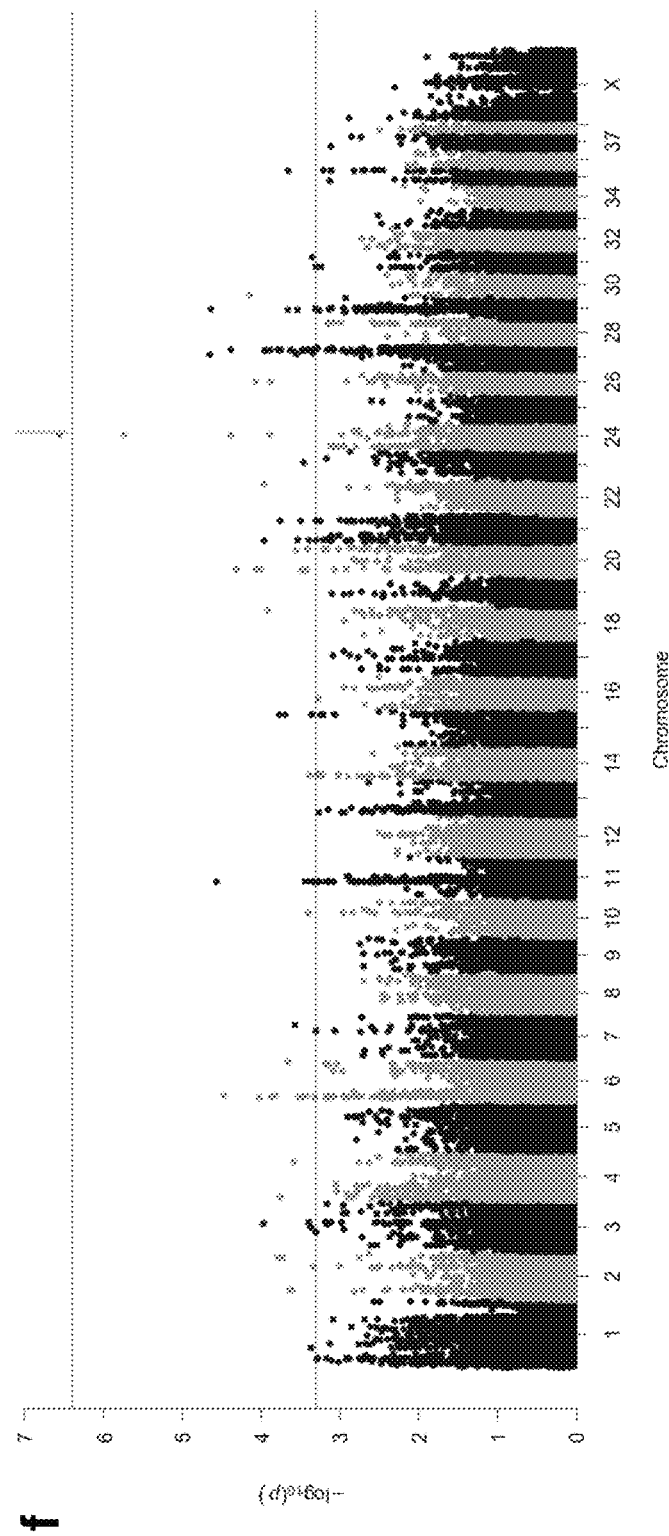

GWAS Identifies 98 Regions Associated with Anterior Cruciate Ligament Rupture:

We tested for association between ACL rupture and SNPs with a MAF >0.05 in the Labrador Retriever breed, controlling for cryptic relatedness and population structure using LMM analysis with three programs, including a penalized multiple regression method for improved detection of weak associations. We identified all SNPs with either significant association based on analysis of 1,000 random phenotype permutations to define genome-wide significance ($P<1.549E-06$ for GCTA, $P<6.097E-07$ for GEMMA and $P<4.35E-07$ for PUMA) or suggestive association ($P<5.00E-04$; FIG. 2) and defined regions of associated using linkage disequilibrium. See Tables 1 and 2. Control dogs were considered phenotype-negative because of the selection criteria used for recruitment. We identified 21,713; 21,754; and 21,861 haplotype blocks in the Labrador Retriever genome with LD windows of 5 Mb, 1 Mb, and 5 kb respectively, yielding a genome-wide significance estimate of $P<2.29E-06$ to $P<2.30E-06$.

TABLE 1

Anterior cruciate ligament rupture associated loci identified by GWAS in the Labrador Retriever, a dog breed with a high disease prevalence

| SNP | chr | Position | P | LMM | Risk allele | f (A) | f (U) | OR | Region start-end | Size (kB) | Genes |
|---|---|---|---|---|---|---|---|---|---|---|---|
| BICF2G630500368 | 24 | 30241088 | 2.76E−07 | 1, 2, 3 | G | 0.83 | 0.66 | 2.56 | 30241088-30245795 | 5 | BPI, LBP, RALGAPB, ADIG, ARHGAP40, SLC32A1, ACTR5, PP1R16B, FAM83D, DHX35 |
| BICF2P1121006 | 18 | 54279578 | 1.11E−05 | 1, 2, 3 | A | 0.63 | 0.42 | 2.28 | No LD | | Many (30 genes) |
| BICF2S2356299 | 27 | 30557856 | 2.21E−05 | 2, 3 | A | 0.43 | 0.27 | 2.03 | No LD | | None |
| BICF2P483191 | 29 | 21601273 | 2.31E−05 | 1, 2, 3 | C | 0.73 | 0.51 | 2.54 | No LD | | SULF1 SLCO5A1, PRDM14, NCOA2, TRAM1 |
| BICF2P50610 | 11 | 32270617 | 2.75E−05 | 3 | A | 0.29 | 0.19 | 1.7 | 31939564-32270617 | 331 | C11H9orf123, PTPRD |
| BICF2P890246 | 9 | 53427907 | 3.23E−05 | 1, 2 | A | 0.16 | 0.36 | 2.99 | 53427907-53432248 | 4 | Many (26 genes) |

TABLE 1-continued

Anterior cruciate ligament rupture associated loci identified by GWAS in the Labrador Retriever, a dog breed with a high disease prevalence

| SNP | chr | Position | P | LMM | Risk allele | f (A) | f (U) | OR | Region start-end | Size (kB) | Genes |
|---|---|---|---|---|---|---|---|---|---|---|---|
| BICF2S23324965 | 6 | 14077648 | 3.36E−05 | 3 | G | 0.68 | 0.60 | 1.42 | 14077648-14092057 | 14 | NPTX2, BAIAP2L1, BRI3, TECPR1, BHLHA15, LMTK2, CCZ1, RSH10B, PMS2, AIMP2, ANKRD61, EIF2AK1, USP42, CYTH3 |
| BICF2P544126 | 24 | 29772193 | 4.09E−05 | 3 | G | 0.94 | 0.87 | 2.28 | 29772193-29794411 | 22 | CTNNBL1, VSTM2L, TTI1, RPRD1B, TGM2, KIAA1755 |
| BICF2P526639 | 27 | 39217437 | 4.12E−05 | 2, 3 | G | 0.23 | 0.12 | 2.18 | 39211186-39217437 | 6 | A2M |
| BICF2P1462185 | 20 | 15053718 | 4.89E−05 | 3 | A | 0.85 | 0.74 | 1.90 | 14838270-15053718 | 215 | EDEM1, ARL8B |
| BICF2P1208798 | 9 | 12671217 | 5.49E−05 | 1, 2 | G | 0.56 | 0.36 | 2.27 | No LD | | EFCAB13, ITGB3, MYL4, CDC27, KANSL1, MAPT, SPPL2C, CRHR1, NSF, WNT3 |
| BICF2G630175389 | 4 | 84260906 | 5.87E−05 | 1, 2 | A | 0.83 | 0.68 | 2.28 | No LD | | CDH10 |
| BICF2S24415473 | 3 | 86974042 | 7.07E−05 | 1, 2 | G | 0.40 | 0.26 | 1.97 | 86948527-86974042 | 26 | STIM2, PGM2, RELL1, C3H4orf19, NWD2 |
| BICF2G630412697 | 30 | 3126573 | 7.22E−05 | 1, 3 | G | 0.96 | 0.86 | 4.23 | No LD | | COR4F22P, COR4F25, COR4F24P, COR4T2P |
| BICF2P498515 | 6 | 75848537 | 7.89E−05 | 1, 2, 3 | A | 0.16 | 0.06 | 3.11 | No LD | | LRRIQ3 |
| BICF2P792911 | 26 | 22894961 | 8.55E−05 | 1, 2, 3 | G | 0.44 | 0.27 | 2.14 | No LD | | TPST2, CRYBBI, CRYBB4 |
| BICF2G630810143 | 6 | 11130832 | 9.46E−05 | 3 | A | 0.44 | 0.32 | 1.72 | 11130832-11177149 | 46 | DTX2, UPK3B, UPK3BL, RASA4, LRWD1, ALKBH4, ORAI2, PRKRIP1, SH2B2, CUX1, MYL10, COL26A1, RABL5, RIS1, CLDN15, ZNHIT1, PLOD3 |
| BICF2P564273 | 3 | 55250188 | 1.07E−04 | 1, 2, 3 | A | 0.70 | 0.52 | 2.16 | No LD | | ACAN, HAPLN3, MFGE8, ABHD2, RLBP1, FANCI, POLG, TRNAR-UCG, RHCG, TICRR, KIF7, PLIN1, PEX11A, WDR93, MESP1, MESP2, ANPEP, AP3S2, ARPIN |
| TIGRP2P297337 | 22 | 58201452 | 1.08E−04 | 1, 2, 3 | A | 0.44 | 0.27 | 2.2 | No LD | | EFNB2, ARGLU1 |
| BICF2G630658881 | 21 | 7582214 | 1.09E−04 | 1, 2, 3 | G | 0.49 | 0.32 | 2.12 | 7581714-8383209 | | JRKL, CCDC82, MAML2, MTMR2, CEP57, FAM76B, SESN3 |

Note:
OR odds ratio calculated from PLINK. LMM Linear mixed model 1 - GCTA, 2 - GEMMA, 3 - PUMA. Data represent the twenty most significant loci of 98 associations with canine ACL rupture. SNP position and genomic regions are based on CanFam 2.0. Genes lists were derived from the SNP locus or LD block with 500 kb flanking regions.

TABLE 2

Anterior cruciate ligament rupture associated SNPs identified by GWAS in the Labrador Retriever, a dog breed with a high disease prevalence

| SNP | chr | Position | P | LMM | Risk Allele | f (A) | f (U) | OR | Region start-end | Genes |
|---|---|---|---|---|---|---|---|---|---|---|
| BICF2G630709791 | 1 | 10788643 | 1.64E−04 | 1 | C | 0.30 | 0.16 | 2.18 | 10788643-11025688 | RTTN, CD226, DOK6 |
| BICF2S23147946 | 1 | 17290917 | 1.74E−04 | 1 | G | 0.28 | 0.15 | 2.19 | No LD | BCL2, PHLPP1, ZCCHC2, TNFRSF11A, KIAA1468, PPIAP1, PIGN |
| BICF2P181859 | 1 | 17840093 | 4.32E−04 | 1 | A | 0.21 | 0.09 | 2.60 | No LD | ZCCHC2, TNFRSF11A, KIAA1468, PPIAP1, PIGN, CDH20 |
| BICF2G630712921 | 1 | 19148000 | 4.94E−04 | 1 | G | 0.46 | 0.32 | 1.87 | 18645187-19148000 | CDH20, MC4R, PMAIP1, CCBE1 |
| BICF2G630713147 | 1 | 19274346 | 4.93E−04 | 1 | A | 0.37 | 0.24 | 1.83 | 19253280-19274346 | MC4R, PMAIP1, CCBE1 |
| BICF2P818099 | 1 | 39021948 | 4.29E−04 | 3 | G | 0.65 | 0.54 | 1.55 | No LD | SF3B5, STX11, TRNAL-UAA, UTRN |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f (A) | f (U) | OR | Region start-end | Genes |
|---|---|---|---|---|---|---|---|---|---|---|
| BICF2S23638642 | 1 | 45229667 | 4.95E-04 | 2 | G | 0.18 | 0.07 | 3.07 | No LD | AKAP12, ZBTB2, RMND1, ARMT1, CCDC170, ESR1, SYNE1 |
| BICF2P206910 | 1 | 46405864 | 3.25E-04 | 2 | C | 0.14 | 0.04 | 4.05 | 46405864-46443183 | MYCT1, VIP, FBX05, MTRF1L, RGS17 |
| BICF2S22959529 | 1 | 46443183 | 1.58E-04 | 1, 2 | C | 0.14 | 0.03 | 4.78 | | |
| BICF2P1054044 | 2 | 20002181 | 2.28E-04 | 3 | G | 0.85 | 0.77 | 1.74 | No LD | MTPAP, MAP3K8, LYZL1, TRNAK-CUU, BAMBI, WAC |
| BICF2S23533020 | 2 | 20501149 | 2.47E-04 | 3 | G | 0.92 | 0.84 | 2.33 | 20288541-20501149 | LYZL1, TRNAK-CUU, BAMBI, WAC, MPP7 |
| BICF2P720951 | 2 | 62500174 | 4.61E-04 | 3 | A | 0.26 | 0.16 | 1.82 | 62252040-62500174 | GPR114, CCDC102A, DOK4, POLR2C, COQ9, CIAPIN1, CCL17, CX3CL1, CCL22, TRNAL-CAG, PLLP, ARL2BP, RSPRY1, FAM192A, CPNE2, NLRC5, HERPUD1, SLC12A3, NUP93, MT2A, MT-III, MT4, BBS2, OGFOD1, NUDT21, AMFR, GNAO1 |
| TIGRP2P31530 | 2 | 80046637 | 1.65E-04 | 2, 3 | G | 0.67 | 0.55 | 1.69 | 80046637-80079758 | C1QB, C1QC, C1QA, EPHA8, ZBTB40, WNT4, CDC42, CELA3B, HSPG2, LDLRAD2, USP48, RAP1GAP, ALPL |
| BICF2P247448 | 2 | 80068322 | 1.48E-04 | 2, 3 | G | 0.68 | 0.55 | 1.67 | | |
| BICF2P1066899 | 2 | 80079758 | 1.65E-04 | 2, 3 | A | 0.67 | 0.55 | 1.69 | | |
| BICF2G630464857 | 2 | 87862734 | 2.00E-04 | 2 | G | 0.14 | 0.04 | 3.69 | No LD | C2H1orf167, AGTRAP, DRAXIN, MAD2L2, FBXO6, FBXO44, FBXO2, PTCHD2, UBIAD1, MTOR, ANGPTL7, EXOSC10, SRM, MASP2, TARDBP, CASZ1, PEX14, DFFA, APITD1, PGD |
| BICF2G630108404 | 3 | 39424250 | 4.96E-04 | 3 | G | 0.24 | 0.13 | 2.06 | 39424250-39517119 | NDN, MKRN3, CHRNA7 |
| BICF2S23148483 | 3 | 39469011 | 4.96E-04 | 3 | G | 0.24 | 0.13 | 2.06 | | |
| BICF2P866702 | 3 | 39517119 | 4.96E-04 | 3 | A | 0.24 | 0.13 | 2.06 | | |
| BICF2P1109077 | 3 | 48873558 | 4.26E-04 | 3 | G | 0.80 | 0.67 | 1.90 | 48873558-48880579 | MCTP2 |
| BICF2P1431921 | 3 | 48878860 | 4.26E-04 | 3 | G | 0.80 | 0.67 | 1.90 | | |
| BICF2P241884 | 3 | 48880579 | 4.26E-04 | 3 | G | 0.80 | 0.67 | 1.90 | | |
| BICF2P564273 | 3 | 55250188 | 1.07E-04 | 1, 2, 3 | A | 0.70 | 0.52 | 2.16 | No LD | ACAN, HAPLN3, MFGE8, ABHD2, RLBP1, FANCI, POLG, TRNAR-UCG, RHCG, TICRR, KIF7, PLIN1, PEX11A, WDR93, MESP1, MESP2, ANPEP, AP3S2, ARPIN |
| TIGRP2P46522 | 3 | 57698908 | 4.01E-04 | 3 | C | 0.70 | 0.54 | 1.91 | 57660110-57698908 | PDE8A, RPS17, CPEBI, AP3B2, FSD2, WHAMM, HOMER2, FAM103A1, C3H5orf40, BTBD1, TM6F1, HDGFRP3, BNC1, SH3GL3 |
| BICF2G630349775 | 3 | 77625147 | 4.26E-04 | 1, 2 | A | 0.18 | 0.07 | 2.90 | No LD | TBC1D1, PGM2, RELL1, C3H4orf19, NWD2 |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f (A) | f (U) | OR | Region start-end | Genes |
|---|---|---|---|---|---|---|---|---|---|---|
| BICF2S2342150 | 3 | 86948527 | 2.91E−04 | 1, 2 | A | 0.40 | 0.27 | 1.83 | 86948527-86974042 | STIM2, TBC1D19, |
| BICF2S24415473 | 3 | 86974042 | 7.07E−05 | 1, 2 | G | 0.40 | 0.26 | 1.97 | | CCKAR, SMIM20, SEL1L3 |
| BICF2G630359517 | 3 | 91944314 | 3.77E−04 | 1, 2 | C | 0.51 | 0.36 | 1.82 | No LD | KCNIP4, PACRGL, SLIT2 |
| BICF2G63058646 | 4 | 9120668 | 1.76E−04 | 1, 2, 3 | G | 0.13 | 0.04 | 3.71 | No LD | SLC35F3, KCNK1, KIAA1804, PCNXL2 |
| BICF2P295392 | 4 | 14536870 | 4.61E−04 | 2 | G | 0.11 | 0.04 | 3.07 | No LD | BICC1, PHYHIPL, FAM13C |
| BICF2G630168473 | 4 | 74924050 | 2.60E−04 | 3 | G | 0.30 | 0.18 | 1.96 | No LD | NUP155, C4H5orf42, NIPBL, SLC1A3 |
| BICF2G630175389 | 4 | 84260906 | 5.87E−05 | 1, 2 | A | 0.83 | 0.68 | 2.28 | No LD | CDH10 |
| BICF2G630810143 | 6 | 11130832 | 9.46E−05 | 3 | A | 0.44 | 0.32 | 1.72 | 11130832-11177149 | DTX2, UPK3B, |
| BICF2G630810159 | 6 | 11177149 | 9.46E−05 | 3 | A | 0.44 | 0.32 | 1.72 | | UPK3BL, RASA4, LRWD1, ALKBH4, ORAI2, PRKRIP1, SH2B2, CUX1, MYL10, COL26A1, RABL5, FIS1, CLDN15, ZNHIT1, PLOD3 |
| BICF2G630810173 | 6 | 11181920 | 1.33E−04 | 3 | G | 0.61 | 0.51 | 1.50 | 11035074-11181920 | SRCRB4D, ZP3, MOGAT3, NAT16 |
| BICF2P170661 | 6 | 11439931 | 3.39E−04 | 3 | A | 0.31 | 0.22 | 1.57 | No LD | VGF, AP1S1, SERPINE1, TRIM56, ACHE, UFSP1, SRRT, TRIP6, SLC12A9, EPHB4 |
| BICF2P1354767 | 6 | 11462695 | 3.02E−04 | 3 | G | 0.48 | 0.38 | 1.53 | 11106977-11462695 | None |
| BICF2P205255 | 6 | 11484772 | 4.75E−04 | 3 | G | 0.54 | 0.45 | 1.43 | No LD | ZAN |
| BICF2P1358119 | 6 | 13131171 | 3.74E−04 | 3 | C | 0.44 | 0.34 | 1.54 | 13131171-13182379 | AZGP1, GJC3, TRIM4, VN2R301P, CYP3A26, CYP3A4, OR0C09, ZSCAN25, FAM200A, ZKSCAN5, ZNF789, ZNF394, TRNAW-CCA, CPSF4, PTCD1, BUD31, PDAP1, ARPC1B, ARPC1A, MYH16, KPNA7, SMURF1, TRRAP, TMEM130 |
| BICF2S23324965 | 6 | 14077648 | 3.36E−05 | 3 | G | 0.68 | 0.60 | 1.42 | 14077648-14092057 | NPTX2, BAIAP2L1, |
| BICF2S22961650 | 6 | 14092057 | 1.53E−04 | 3 | G | 0.68 | 0.61 | 1.35 | | BRI3, TECPR1, BHLHA15, LMTK2, CCZ1, RSPH10B, PMS2, AIMP2, ANKRD61, EIF2AK1, USP42, CYTH3 |
| BICF2P498515 | 6 | 75848537 | 7.89E−05 | 1, 2, 3 | A | 0.16 | 0.06 | 3.11 | No LD | LRRIQ3 |
| BICF2P1072682 | 7 | 53407178 | 4.09E−04 | 1, 2, 3 | C | 0.28 | 0.14 | 2.42 | No LD | None |
| BICF2P1090079 | 7 | 64389761 | 1.56E−04 | 1, 3 | C | 0.47 | 0.31 | 1.94 | No LD | CDH2, CHST9 |
| BICF2P1208798 | 9 | 12671217 | 5.49E−05 | 1, 2 | G | 0.56 | 0.36 | 2.27 | No LD | EFCAB13, ITGB3, MYL4, CDC27, KANSL1, MAPT, SPPL2C, CRHR1, NSF, WNT3 |
| BICF2P890246 | 9 | 53427907 | 3.23E−05 | 1, 2 | A | 0.16 | 0.36 | 2.99 | 53427907-53432248 | KCNT1, SOHLH1, |
| BICF2P139678 | 9 | 53432248 | 1.75E−04 | 1, 2 | A | 0.83 | 0.65 | 2.71 | | LCN9, GLT6D1, LCN1, ABO, SURF6, MED22, RPL7A, SURF1, SURF2, SURF4, C9H9orf96, REXO4, ADAMTS13, CACFD1, SLC2A6, TMEM8C, ADAMTSL2, FAM163B, DBH, SARDH, VAV2, BRD3, WDR5, RXRA |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f(A) | f(U) | OR | Region start-end | Genes |
|---|---|---|---|---|---|---|---|---|---|---|
| BICF2S23113199 | 10 | 46246942 | 3.57E−04 | 1, 3 | A | 0.63 | 0.46 | 1.95 | No LD | AFF3, REV1, EIF5B, TXNDC9, LYG1, LYG2, MRPL30, MITD1, TRNAK-CUU, LIPT1, TSGA10 |
| BICF2P401973 | 10 | 65344772 | 3.79E−04 | 1 | G | 0.84 | 0.71 | 2.23 | No LD | FAM161A, CCT4, COMMD1, TRNAE-UUC, TMEM17, EHBP1 |
| BICF2P454456 | 11 | 32175491 | 4.77E−04 | 3 | A | 0.19 | 0.13 | 1.62 | 31831896-32175491 | C11H9orf123, PTPRD |
| BICF2P50610 | 11 | 32270617 | 2.75E−05 | 3 | A | 0.29 | 0.19 | 1.70 | 31939564-32270617 | C11H9orf123, PTPRD |
| BICF2P531097 | 11 | 32908558 | 3.58E−04 | 3 | A | 0.44 | 0.29 | 1.92 | 32908558-32922914 | PTPRD |
| BICF2P1290820 | 11 | 32922914 | 4.19E−04 | 3 | G | 0.44 | 0.30 | 1.91 | | |
| BICF2P65003 | 12 | 40691540 | 3.15E−04 | 2 | G | 0.71 | 0.61 | 1.61 | 40691540-41066621 | SENP6, MYO6, IMPG1 |
| BICF2G630606359 | 13 | 13352804 | 4.61E−04 | 2 | G | 0.69 | 0.57 | 1.67 | 13352804-13503950 | NUDCD1, ENY2, PKHD1L1, EBAG9, SYBU |
| BICF2S23620879 | 14 | 10265645 | 4.05E−04 | 3 | C | 0.5 | 0.37 | 1.71 | 9796003-10265645 | COPG2, MEST, CEP41, CPA1, CPA5, CPA4, CPA2, SSMEM1, TMEM209, KLDHC10, TRNAM-CAU, ZC3HC1, UBE2H, NRF1, SMKR1, STRIP2, AHCYL2, SMO, TSPAN33, TNPO3, IRF5, KCP, ATP6V1F, FLNC |
| BICF2G630519882 | 14 | 11686985 | 4.99E−04 | 3 | A | 0.49 | 0.36 | 1.74 | 11675474-11686985 | LRRC4, SND1, PAX4, FSCN3, ARF5, GCC1, ZNF800, GRM8 |
| BICF2P594418 | 15 | 58424953 | 4.48E−04 | 2 | A | 0.19 | 0.10 | 2.07 | No LD | FAM198B, TMEM144, RXFP1, ETFDH, PPID, FNIP2 |
| BICF2G630422966 | 15 | 58852255 | 4.41E−04 | 3 | A | 0.41 | 0.28 | 1.80 | 58852255-58978372 | RAPGEF2, C15H4orf45 |
| BICF2G630422956 | 15 | 58891376 | 4.41E−04 | 3 | A | 0.41 | 0.28 | 1.80 | | |
| BICF2G630422900 | 15 | 58967776 | 2.04E−04 | 3 | G | 0.37 | 0.24 | 1.87 | | |
| BICF2G630422895 | 15 | 58978372 | 1.69E−04 | 3 | A | 0.37 | 0.24 | 1.89 | | |
| BICF2P880005 | 17 | 20749191 | 2.22E−04 | 1, 2 | G | 0.44 | 0.31 | 1.75 | No LD | KLHL29 |
| BICF2P1121006 | 18 | 54279578 | 1.11E−04 | 1, 2, 3 | A | 0.63 | 0.42 | 2.28 | No LD | CCDC87, DPP3, NPAS4, SLC29A2, BRMS1, RIN1, CD248, CNIH2, RAB1B, KLC2, PACS1, GAL3ST3, SART1, TSGA10IP, C18H11orf68, FOSL1, CTSW, CFL1, SNX32, OVOL1, RNASEH2C, KAT5, RELA, SIPA1, PCNXL3, MAP3K11, KCNK7, EHBP1L1, LTBP3, SCYL1 |
| BICF2P888055 | 20 | 13815084 | 3.25E−04 | 3 | A | 0.73 | 0.62 | 1.71 | No LD | None |
| BICF2P582174 | 20 | 14124824 | 3.76E−04 | 3 | C | 0.82 | 0.73 | 1.61 | 14118014-14124824 | None |
| TIGRP2P270462 | 20 | 15036973 | 8.51E−05 | 3 | G | 0.85 | 0.75 | 1.88 | 14838270-15053718 | EDEM1, ARL8B |
| BICF2P716829 | 20 | 15048191 | 9.85E−05 | 3 | G | 0.85 | 0.75 | 1.86 | | |
| BICF2P1462185 | 20 | 15053718 | 4.90E−05 | 3 | A | 0.85 | 0.74 | 1.90 | | |
| BICF2P178583 | 20 | 30190042 | 1.41E−04 | 1, 2 | G | 0.48 | 0.31 | 2.09 | 30039696-30190042 | ADAMTS9, PRICKLE2, PSMD6, ATXN7, THOC7, SNTN, SYNPR |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f (A) | f (U) | OR | Region start-end | Genes |
|---|---|---|---|---|---|---|---|---|---|---|
| BICF2S2328420 | 20 | 51150968 | 2.77E−04 | 3 | G | 0.75 | 0.60 | 1.96 | No LD | OR12C09, OR4B10, ADGRE2, ZNF333, EMR3, CLEC17A, NDUFB7, TECR, DNAJB1, GIPC1, PTGER1, PKN1, DDX39A, CD97, LPHN1, ASF1B, PRKACA, SAMD1, PALM3, IL27RA, RLN3, RFX1, DCAF15, PODNL1, CC2D1A, C20H19orf57, NANOS3, ZSWIM4, C20H19orf53 |
| BICF2P420488 | 20 | 52326317 | 3.84E−04 | 3 | G | 0.85 | 0.75 | 1.84 | 51873051-52326317 | MRI1, CCDC130, CACNA1A, NACC1, NFIX, DAND5, RAD23A, CALR, SYCE2, KLF1, MAST1, RNASEH2A, PRDX2, HOOK2, BEST2, TNPO2, WDR83, MAN2B1, ZNF791, ZNF709, ACP5, ELOF1 |
| TIGRP2P277002 | 20 | 55563965 | 2.25E−04 | 1, 2 | A | 0.25 | 0.10 | 2.98 | No LD | INSR, ARHGEF18, PEX11G, C20H19orf45, MCOLN1, PNPLA6, CAMSAP3, XAB2, PCP2, STXBP2, RETN, C20H19orf59, FCER2, CLEC4G, CD209, EVI5L, LRRC8E, MAP2K7, SNAPC2, CTXN1, TIMM44, ELAVL1, FBN3, CERS4, CD320, RAB11B, MARCH2, PRAM1, ZNF414, MYO1F |
| BICF2P111342 | 21 | 7150110 | 1.25E−04 | 1, 2 | A | 0.31 | 0.18 | 2.04 | No LD | None |
| BICF2G630658881 | 21 | 7582214 | 1.09E−04 | 1, 2, 3 | G | 0.49 | 0.32 | 2.12 | 7582214-8382709 | JRKL, CCDC82, MAML2, MTMR2, CEP57, FAM76B, SESN3 |
| BICF2G630658668 | 21 | 8205285 | 4.03E−04 | 3 | G | 0.49 | 0.32 | 2.00 | | |
| BICF2G630658620 | 21 | 8382709 | 2.90E−04 | 3 | G | 0.50 | 0.33 | 2.02 | | |
| BICF2G630658768 | 21 | 8033283 | 4.09E−04 | 1, 2 | C | 0.27 | 0.14 | 2.28 | 8033283-8061623 | JRKL, CCDC82, MAML2, MTMR2, CEP57, FAM76B, SESN3 |
| BICF2G630658756 | 21 | 8040746 | 4.73E−04 | 1 | A | 0.26 | 0.13 | 2.30 | | |
| BICF2G630658723 | 21 | 8061623 | 4.09E−04 | 1, 2 | G | 0.27 | 0.14 | 2.28 | | |
| BICF2S2442023 | 21 | 43533585 | 3.19E−04 | 3 | G | 0.50 | 0.34 | 1.93 | 43507320-43533585 | NUCB2, NCR3LG1, KCNJ11, ABCC8, USH1C, OTOG, MYOD1, KCNC1, SERGEF, TPH1, SAAL1, SAA1, HPS5, GTF2H1, LDHA |
| BICF2S2361376 | 21 | 43752575 | 1.76E−04 | 1, 2, 3 | A | 0.60 | 0.42 | 1.97 | 43752575-43808389 | LDHC, TSG101, UEVLD, SPTY2D1, TMEM86A, IGSF22, PTPN5 |
| BICF2P321064 | 21 | 44627903 | 1.66E−04 | 1, 2, 3 | G | 0.38 | 0.24 | 1.99 | No LD | MRGPRX2, ZDHHC13, CSRP3, E2F8, NAV2 |
| TIGRP2P293361 | 22 | 42354230 | 2.27E−04 | 2 | A | 0.49 | 0.36 | 1.74 | No LD | SLITRK5 |
| TIGRP2P297337 | 22 | 58201452 | 1.08E−04 | 1, 2, 3 | A | 0.44 | 0.27 | 2.20 | No LD | EFNB2, ARGLU1 |
| BICF2G630375268 | 23 | 33376383 | 3.48E−04 | 3 | A | 0.74 | 0.63 | 1.75 | No LD | TEMEM108, BFSP2, CDV3, TOPBP1, TF, SRPRB, RAB6B, |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f (A) | f (U) | OR | Region start-end | Genes |
|---|---|---|---|---|---|---|---|---|---|---|
| BICF2S23730962 | 23 | 53809871 | 2.93E−04 | 2 | A | 0.87 | 0.78 | 1.88 | No LD | C23H3orf36, SLCO2A1 TIPARP, LEKR1, CCNL1, VEPH1, PTX3 |
| BICF2G630502225 | 24 | 23992936 | 4.86E−04 | 2 | G | 0.92 | 0.81 | 2.84 |  | BPI LBP, |
| BICF2G630500368 | 24 | 30241088 | 2.76E−07 | 1, 2, 3 | G | 0.83 | 0.66 | 2.56 | 30241088-30245795 | RALGAPB, ADIG, |
| BICF2G630500363 | 24 | 30245795 | 1.82E−06 | 1, 2, 3 | G | 0.80 | 0.62 | 2.44 |  | ARHGAP40, SLC32A1, ACTR5, PPP1R16B, FAM83D, DHX35 |
| BICF2G630500835 | 24 | 29648925 | 1.29E−04 | 2, 3 | A | 0.79 | 0.67 | 1.90 | No LD | CTNNBL1, VSTM2L, TTI1, RPRD1B, TGM2, KIAA1755 |
| BICF2P544126 | 24 | 29772193 | 4.09E−05 | 3 | G | 0.94 | 0.87 | 2.28 | 29772193-29794411 | BPI LBP, |
| BICF2S24111418 | 24 | 29794411 | 4.09E−05 | 3 | A | 0.94 | 0.87 | 2.28 |  | RALGAPB, ADIG, ARHGAP40, SLC32A1, ACTR5, PPP1R16B, FAM83D, DHX35, CTNNBL1, VSTM2L, TTI1, RPRD1B, TGM2, KIAA1755 |
| BICF2G630799191 | 26 | 22848912 | 1.33E−04 | 3 | G | 0.61 | 0.45 | 1.92 | No LD | ADRBK2, MYO18B, SEZ6L, ASPHD2, HPS4, SRRD, TFIP11, TPST2, CRYBB1, CRYBA4 |
| BICF2P792911 | 26 | 22894961 | 8.55E−05 | 1, 2, 3 | G | 0.44 | 0.27 | 2.14 | No LD | ADRBK2, MYO18B, SEZ6L, ASPHD2, HPS4, SRRD, TFIP11, TPST2, CRYBB1, CRYBA4 |
| BICF2S2356299 | 27 | 30557856 | 2.21E−05 | 2, 3 | A | 0.43 | 0.27 | 2.03 | No LD | AEBP2, PLEKHA5 |
| BICF2P1332722 | 27 | 30603252 | 2.19E−04 | 1, 2 | G | 0.78 | 0.60 | 2.33 | No LD | AEBP2, PLEKHA5 |
| BICF2P1047447 | 27 | 31108106 | 2.80E−04 | 3 | A | 0.52 | 0.38 | 1.75 | No LD | CAPZA3, PLCZ1, PIK3C2G |
| BICF2P487060 | 27 | 33778510 | 4.55E−04 | 3 | C | 0.40 | 0.27 | 1.81 | 33778510-33809600 | MGST1, SLC15A5, DERA, STRAP, EPS8, PTPRO |
| BICF2P599881 | 27 | 35600038 | 2.66E−04 | 3 | G | 0.85 | 0.74 | 1.97 | No LD | PLBD1, ATF7IP, GRIN2B |
| BICF2P1410038 | 27 | 37697040 | 3.33E−04 | 3 | C | 0.70 | 0.56 | 1.82 | No LD | BCL2L14, ETV6, TAS2R42, CAFA-T2R67, CAFA-T2R43, CAFA-T2R12, TAS2R10, TAS2R9, TAS2R8, TAS2R7, CSDA, STYK1, MAGOHB, KLRA1 |
| BICF2S23535135 | 27 | 37814333 | 1.13E−04 | 3 | A | 0.31 | 0.20 | 1.83 | No LD | BCL2L14, ETV6, TAS2R42, CAFA-T2R67, CAFA-T2R43, CAFA-T2R12, TAS2R10, TAS2R9, TAS2R8, TAS2R7, CSDA, STYK1, MAGOHB, KLRA1 |
| TIGRP2P355298 | 27 | 39134291 | 1.31E−04 | 3 | G | 0.74 | 0.57 | 2.16 | No LD | KLRK1, KLRD1, GABARAPL1, TMEM52B, OLR1, CLEC7A, CLEC1A, CLEC9A, CLEC12A, KLRF2, CD69, CLEC2D, KLRB1, PZP |
| BICF2S23255928 | 27 | 39211186 | 1.10E−04 | 2, 3 | A | 0.23 | 0.13 | 2.07 | 39211186-39217437 | A2M |
| BICF2P526639 | 27 | 39217437 | 4.12E−05 | 2, 3 | G | 0.23 | 0.12 | 2.18 |  |  |
| BICF2S23152419 | 27 | 39428263 | 1.77E−05 | 3 | A | 0.79 | 0.64 | 2.13 | 39428263-39445306 | KLRG1, M6PR, |
| BICF2P491441 | 27 | 39434491 | 3.34E−04 | 3 | G | 0.78 | 0.63 | 2.06 |  | PHC1, A2ML1 |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f (A) | f (U) | OR | Region start-end | Genes |
|---|---|---|---|---|---|---|---|---|---|---|
| TIGRP2P355396 | 27 | 39445306 | 3.34E−04 | 3 | A | 0.78 | 0.63 | 2.06 | | |
| BICF2P337576 | 27 | 39463031 | 2.35E−04 | 3 | G | 0.70 | 0.55 | 1.92 | 39346073-39511019 | RMKLB |
| BICF2P794117 | 27 | 39511019 | 3.76E−04 | 3 | C | 0.71 | 0.56 | 2.00 | | |
| BICF2P155064 | 27 | 39526004 | 4.68E−04 | 3 | G | 0.21 | 0.14 | 4.78 | No LD | None |
| BICF2P992747 | 27 | 39580957 | 1.65E−04 | 3 | A | 0.77 | 0.62 | 2.07 | No LD | MFAP5 |
| BICF2S23652189 | 27 | 39644847 | 3.99E−04 | 3 | G | 0.31 | 0.21 | 1.64 | 39606871-39644847 | AICDA, APOBEC1, DPPA3 |
| TIGRP2P362234 | 28 | 41376035 | 3.71E−04 | 2 | G | 0.87 | 0.74 | 2.37 | 41376035-41377128 | MGMT, EBF, GLRX3 |
| BICF2S23346408 | 28 | 41377128 | 1.25E−04 | 1, 2 | A | 0.87 | 0.73 | 2.53 | | |
| BICF2S23713161 | 29 | 20562935 | 4.59E−04 | 2 | G | 0.75 | 0.63 | 1.74 | No LD | CPA6, PREX2, C29H8orf34 |
| BICF2S23410873 | 29 | 20672864 | 2.18E−04 | 2, 3 | C | 0.82 | 0.66 | 2.35 | 20672864-20703202 | CPA6, PREX2, C29H8orf34 |
| BICF2P1135545 | 29 | 20703202 | 2.81E−04 | 2, 3 | A | 0.82 | 0.67 | 2.31 | | |
| BICF2P483191 | 29 | 21601273 | 2.31E−05 | 1, 2, 3 | C | 0.73 | 0.51 | 2.54 | No LD | SULF1, SLCO5A1, PRDM14, NCOA2, TRAM1 |
| BICF2P139173 | 29 | 22067666 | 3.59E−04 | 2 | A | 0.50 | 0.36 | 1.79 | 22050835-22191229 | SULF1, SLCO5A1, PRDM14, NCOA2, TRAM1 |
| BICF2P361907 | 29 | 22191229 | 3.47E−04 | 2 | G | 0.50 | 0.36 | 1.75 | | |
| BICF2P456086 | 29 | 23130206 | 4.85E−04 | 3 | A | 0.88 | 0.71 | 3.04 | No LD | XKR9, EYA1 |
| BICF2P662502 | 29 | 26040013 | 3.24E−04 | 1, 2 | G | 0.90 | 0.73 | 2.87 | No LD | JPH1, GDAP1, PI15, CRISPLD1 |
| BICF2G630412697 | 30 | 3126573 | 7.22E−05 | 1, 3 | G | 0.96 | 0.86 | 4.23 | No LD | COR4F22P, COR4F25, COR4F24P, COR4T2P |
| BICF2S2356993 | 31 | 12920807 | 2.25E−04 | 2, 3 | A | 0.25 | 0.14 | 2.04 | No LD | None |
| BICF2P287265 | 31 | 30555902 | 4.38E−04 | 3 | G | 0.96 | 0.87 | 3.38 | No LD | MIS18A, MRAP, URB1, EVA1C, C31H21orf59, SYNJ1, PAXBP1, C31H21orf62, OLIG2, OLIG1, DONSON, ATP5O, IFNAR2, IL10RB |
| BICF2S23054250 | 35 | 26868731 | 2.20E−04 | 2, 3 | A | 0.49 | 0.33 | 1.97 | No LD | LRRC16A, SCGN, HIST1H2AA, HIST1H2BA, SLC17A4, SLC17A1, TRIM38, HFE, HIST1H1T, BTN2A2, BTN1A1 |
| BICF2P1086740 | 37 | 26916351 | 4.34E−04 | 2 | G | 0.41 | 0.24 | 2.18 | No LD | SMARCAL1, RPL37A, IGFBP2, IGFBP5, TNP1 |
| BICF2P708698 | 37 | 26924473 | 1.53E−04 | 2 | A | 0.63 | 0.45 | 2.06 | No LD | SMARCAL1, RPL37A, IGFBP2, IGFBP5, TNP1 |

Note:
OR odds ratio calculated from PLINK. LMM Linear mixed model 1 - GCTA, 2 - GEMMA, 3 - PUMA. SNP position and genomic regions are based on CanFam 2.0.

TABLE 3

Statistical Power and odds ratio correction for anterior cruciate ligament rupture GWAS risk loci identified by GEMMA in the Labrador Retriever

| SNP | CFA | MAF | Beta | Significance | OR | f (u) | Power | Corrected OR | Corrected Power | INPower Estimated number of loci |
|---|---|---|---|---|---|---|---|---|---|---|
| BICF2S23638642 | 1 | 0.116 | 0.2327823 | 4.95E−04 | 3.07 | 0.07 | 0.986 | 1.38 | 0.188 | 6.1 |
| BICF2S22959529 | 1 | 0.07595 | 0.3139731 | 1.58E−04 | 4.78 | 0.03 | 0.991 | 1.83 | 0.304 | 3.9 |
| BICF2P247448 | 2 | 0.3957 | −0.1791686 | 1.48E−04 | 1.67 | 0.55 | 0.835 | 1.23 | 0.224 | 2.6 |
| BICF2G630464857 | 2 | 0.08439 | 0.3041543 | 2.00E−04 | 3.69 | 0.04 | 0.976 | 1.58 | 0.229 | 3.7 |
| BICF2P564273 | 3 | 0.4072 | −0.173683 | 1.07E−04 | 2.16 | 0.52 | 0.993 | 1.47 | 0.611 | 3.5 |
| BICF2G630349775 | 3 | 0.1181 | 0.2355141 | 4.26E−04 | 2.9 | 0.07 | 0.975 | 1.37 | 0.181 | 5.5 |
| BICF2S24415473 | 3 | 0.3165 | 0.1940324 | 7.07E−05 | 1.97 | 0.26 | 0.963 | 1.5 | 0.594 | 2.0 |
| BICF2G630359517 | 3 | 0.4198 | 0.1503946 | 3.77E−04 | 1.82 | 0.36 | 0.937 | 1.2 | 0.182 | 6.2 |
| BICF2G63058646 | 4 | 0.07806 | 0.3008072 | 1.76E−04 | 3.71 | 0.04 | 0.977 | 1.62 | 0.251 | 4.1 |

TABLE 3-continued

Statistical Power and odds ratio correction for anterior cruciate ligament rupture
GWAS risk loci identified by GEMMA in the Labrador Retriever

| SNP | CFA | MAF | Beta | Significance | OR | f (u) | Power | Corrected OR | Corrected Power | INPower Estimated number of loci |
|---|---|---|---|---|---|---|---|---|---|---|
| BICF2P295392 | 4 | 0.06962 | 0.2949176 | 4.61E−04 | 3.07 | 0.04 | 0.908 | 1.39 | 0.138 | 5.9 |
| BICF2G630175389 | 4 | 0.2616 | −0.2019631 | 5.87E−05 | 2.28 | 0.68 | 0.984 | 1.69 | 0.773 | 2.3 |
| BICF2P498515 | 6 | 0.09958 | 0.2861419 | 7.89E−05 | 3.11 | 0.06 | 0.978 | 1.93 | 0.573 | 3.4 |
| BICF2P1072682 | 7 | 0.1957 | 0.2030288 | 4.09E−04 | 2.42 | 0.14 | 0.986 | 1.3 | 0.208 | 4.1 |
| BICF2P1208798 | 9 | 0.4388 | 0.2050435 | 5.49E−05 | 2.27 | 0.36 | 0.998 | 1.7 | 0.87 | 1.9 |
| BICF2P890246 | 9 | 0.2764 | −0.2119253 | 3.23E−05 | 2.99 | 0.36 | 1 | 2.19 | 0.996 | 2.5 |
| BICF2P65003 | 12 | 0.3481 | −0.2006769 | 3.15E−04 | 1.61 | 0.61 | 0.75 | 1.16 | 0.134 | 2.5 |
| BICF2G630606359 | 13 | 0.3825 | −0.1598137 | 4.61E−04 | 1.67 | 0.57 | 0.827 | 1.16 | 0.137 | 4.8 |
| BICF2P594418 | 15 | 0.1414 | 0.2242702 | 4.48E−04 | 2.07 | 0.1 | 0.84 | 1.24 | 0.129 | 4.6 |
| BICF2P880005 | 17 | 0.3671 | 0.1722047 | 2.22E−04 | 1.75 | 0.31 | 0.89 | 1.21 | 0.186 | 4.0 |
| BICF2P1121006 | 18 | 0.4916 | −0.209966 | 1.11E−04 | 2.28 | 0.42 | 0.998 | 1.5 | 0.663 | 1.6 |
| BICF2P178583 | 20 | 0.3776 | 0.176725 | 1.41E−04 | 2.09 | 0.31 | 0.989 | 1.36 | 0.408 | 3.4 |
| TIGRP2P277002 | 20 | 0.1624 | 0.2345241 | 2.25E−04 | 2.98 | 0.1 | 0.996 | 1.45 | 0.301 | 3.0 |
| BICF2P111342 | 21 | 0.05907 | 0.2031308 | 1.25E−04 | 2.04 | 0.18 | 0.946 | 1.38 | 0.34 | 3.1 |
| BICF2G630658881 | 21 | 0.3903 | 0.1872034 | 1.09E−04 | 2.12 | 0.32 | 0.991 | 1.45 | 0.559 | 2.0 |
| BICF2G630658768 | 21 | 0.1899 | 0.2129482 | 4.09E−04 | 2.28 | 0.14 | 0.97 | 1.28 | 0.189 | 3.9 |
| BICF2S2361376 | 21 | 0.4873 | 0.1678988 | 1.76E−04 | 1.97 | 0.42 | 0.979 | 1.28 | 0.304 | 3.8 |
| BICF2P321064 | 21 | 0.2975 | 0.1845238 | 1.66E−04 | 1.99 | 0.24 | 0.962 | 1.29 | 0.266 | 3.7 |
| TIGRP2P293361 | 22 | 0.4156 | 0.1686531 | 2.27E−04 | 1.74 | 0.36 | 0.897 | 1.21 | 0.195 | 4.0 |
| TIGRP2P297337 | 22 | 0.3397 | 0.1873248 | 1.08E−04 | 2.2 | 0.27 | 0.993 | 1.48 | 0.573 | 2.3 |
| BICF2S23730962 | 23 | 0.1857 | −0.2162607 | 2.93E−04 | 1.88 | 0.78 | 0.789 | 1.22 | 0.152 | 3.8 |
| BICF2G630502225 | 24 | 0.1435 | −0.223976 | 4.86E−04 | 2.84 | 0.81 | 0.978 | 1.35 | 0.254 | 4.4 |
| BICF2G630500835 | 24 | 0.2827 | −0.1744313 | 1.29E−04 | 1.9 | 0.67 | 0.912 | 1.33 | 0.332 | 4.4 |
| BICF2G630500368 | 24 | 0.27 | −0.2641268 | 2.76E−07 | 2.56 | 0.66 | 0.997 | 2.44 | 0.995 | 0.8 |
| BICF2P792911 | 26 | 0.3432 | 0.1878882 | 8.55E−05 | 2.14 | 0.27 | 0.989 | 1.53 | 0.645 | 2.2 |
| BICF2S2356299 | 27 | 0.339 | 0.1673825 | 2.21E−04 | 2.03 | 0.27 | 0.977 | 1.71 | 0.842 | 4.2 |
| BICF2P1332722 | 27 | 0.3228 | −0.1794126 | 2.19E−04 | 2.33 | 0.6 | 0.996 | 1.34 | 0.378 | 3.8 |
| BICF2P526639 | 27 | 0.1695 | 0.2271469 | 4.12E−05 | 2.18 | 0.12 | 0.927 | 1.71 | 0.626 | 3.5 |
| BICF2S23346408 | 28 | 0.211 | −0.2180301 | 1.25E−04 | 2.53 | 0.73 | 0.989 | 1.53 | 0.55 | 2.2 |
| BICF2S23713161 | 29 | 0.3186 | −0.1592704 | 4.59E−04 | 1.74 | 0.63 | 0.85 | 1.18 | 0.152 | 6.2 |
| BICF2S23410873 | 29 | 0.2722 | −0.17516 | 2.18E−04 | 2.35 | 0.66 | 0.992 | 1.34 | 0.351 | 4.6 |
| BICF2P483191 | 29 | 0.3948 | −0.2013067 | 2.31E−05 | 2.54 | 0.51 | 1 | 2.02 | 0.982 | 2.3 |
| BICF2P361907 | 29 | 0.4198 | 0.1766305 | 3.47E−04 | 1.75 | 0.36 | 0.903 | 1.19 | 0.17 | 2.8 |
| BICF2P662502 | 29 | 0.2025 | −0.1924562 | 3.24E−04 | 2.87 | 0.73 | 0.997 | 1.39 | 0.372 | 4.9 |
| BICF2S2356993 | 31 | 0.1857 | 0.2003128 | 2.25E−04 | 2.04 | 0.14 | 0.907 | 1.27 | 0.18 | 4.7 |
| BICF2S23054250 | 35 | 0.3945 | 0.1628769 | 2.20E−04 | 1.97 | 0.33 | 0.975 | 1.26 | 0.258 | 4.1 |
| BICF2P1086740 | 37 | 0.3143 | 0.1743002 | 4.34E−04 | 2.18 | 0.24 | 0.989 | 1.26 | 0.227 | 4.1 |
| BICF2P708698 | 37 | 0.4768 | −0.1611546 | 1.53E−04 | 2.06 | 0.45 | 0.989 | 1.33 | 0.389 | 4.1 |

Note:
OR odds ratio calculated from PLINK. Corrected OR was calculated using an approximate conditional likelihood approach (Ghosh A, Zou F, Wright FA. Estimating odds ratios in genome scans: An approximate conditional likelihood appraoch. Am J Human Genet. 2008;82: 1064-1074). GWAS data were derived using GEMMA. For each risk locus detected by GEMMA, the total number of risk loci was estimated using INPower (Park J-HM, Wacholder S, Gail M, Peters U, Jacobs KB, Chanock SJ, et al. Estimation of effect size distribution from genome-wide association studies and implications for future discoveries. Nat Genet. 2010;42: 570-575).

Figure 3:
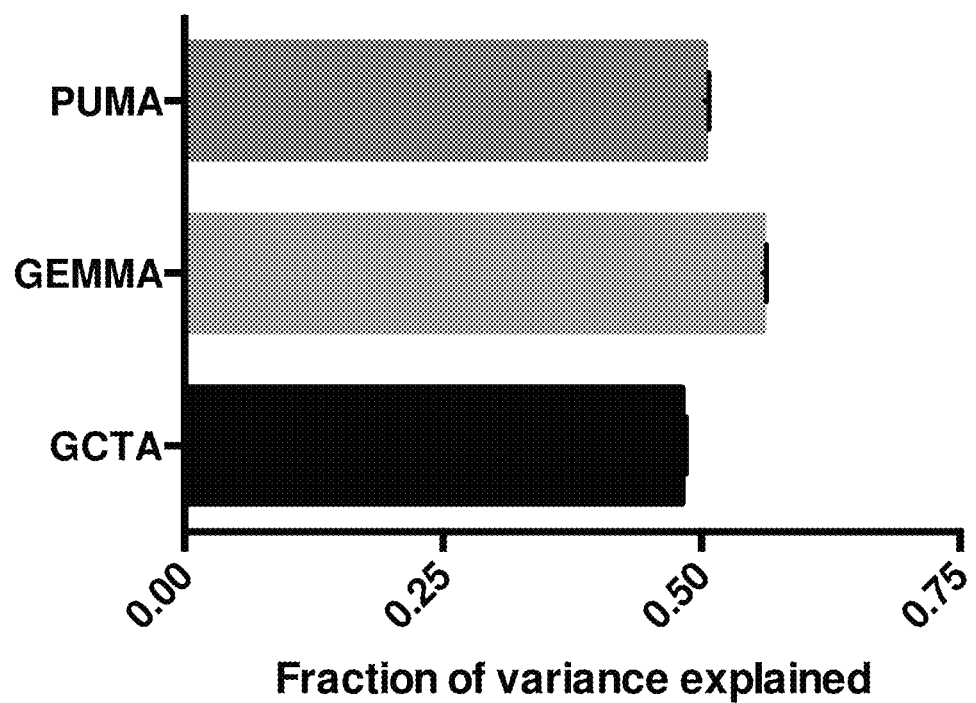
FIG. 3 is a graph showing that phenotype variance was explained to a large degree by the associate genomic loci. Loci identified by linear mixed model (LMM) analysis were broadly defined as SNPs with $r^2>0.5$ within 5 Mb of the peak SNP. For GCTA, 36 loci in 72.7 Mb of the genome explained 48.09% of the phenotypic variance. For GEMMA, 47 loci in 82.7 Mb of the genome explained 55.88% of the phenotypic variance. For PUMA, 65 loci in 86.58 Mb of the genome explained 50.28% of the phenotypic variance in the ACL rupture trait.

With the Labrador Retriever breed, associated regions (P<5.0E−04) explained the approximately half of the phenotypic variance in the ACL rupture trait (FIG. 3). For GCTA, 36 loci in 72.7 Mb of the genome explained 48.09% of the phenotypic variance. For GEMMA, 47 loci in 82.7 Mb of the genome explained 55.88% of the phenotypic variance. For PUMA, 65 loci in 86.58 Mb of the genome explained 50.28% of the phenotypic variance in the ACL rupture trait.

We identified 129 SNPs associated with canine ACL rupture. By using LD clumping, we found that these SNPs reside in 98 loci. Five of these regions were located in uncharacterized or non-coding regions of the genome. A SNP on CFA24 met genome-wide significance for LMM association analysis with GEMMA and PUMA, but not GCTA (P=3.63E−06). This SNP resides in a 5 kB haplotype block with two other SNPs. Ten genes are located within the locus defined by 500 kB flanking regions including bactericidal/permeability-increased protein (BPI), lipopolysaccharide binding protein (LBP), Ral GTPase activation protein beta subunit (RALGAPB), adipogenin (ADIG), rho GTPase activating protein 40 (ARHGAP40), solute carrier family 32, member 1 (SLC32A1), ARP5 actin-related protein 5 (ACTR5), protein phosphatase 1, regulatory subunit 16B (PPP1R16B), family with sequence similarity 83, member D (FAM83D), and DEAH (Asp-Glu-Ala-His; SEQ. ID. NO: 1) box polypeptide 35 (DHX35). Although many risk loci contained large numbers of genes, five loci did not (Table 1, Table 2), suggesting these SNPs may have a regulatory function on gene expression (rSNPs).

Power analysis of our GWAS data set using INPower estimates that 172 loci explain the genetic contribution to ACL rupture in the Labrador Retriever. See Table 3.

Figure 4:
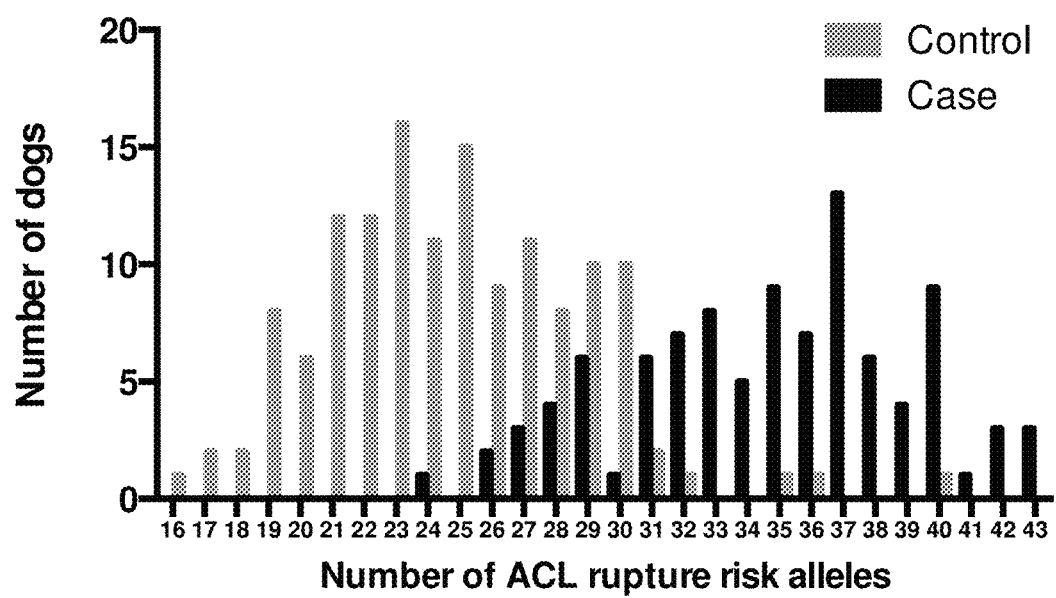
FIG. 4 and FIG. 5 show that genetic risk scoring using GWAS associated loci from linear mixed model analysis with GEMMA predicts ACL rupture disease risk in both case and control Labrador Retriever dogs.
Figure 5:
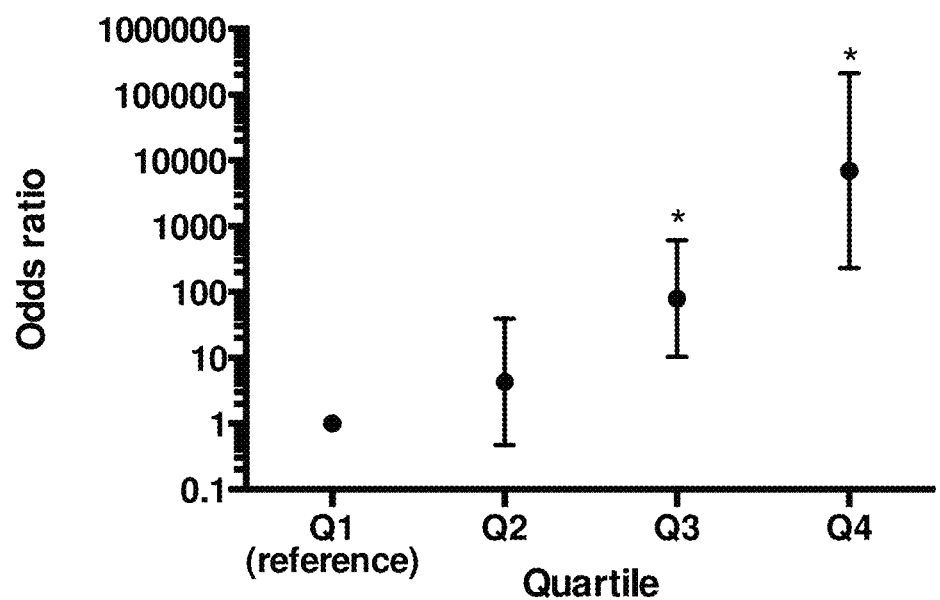

Risk Loci Clearly Distinguish ACL Rupture Cases from Controls:

To evaluate the cumulative effects of associated ACL rupture risk loci, we used a genetic risk scoring approach using a simple allele count (cGRS) or a weighted approach (wGRS). We found significant differences in the number of risk alleles in cases and controls for GCTA (P<2.2E−16), GEMMA (P<2.2E−16), and PUMA (P<2.2E−16) (Table 4), with a shift to increased numbers of risk alleles in the cases. See FIGS. 4 and 5. When the odds ratios according to the wGRS quartiles for each LMM were calculated, there was a significant increase in ACL rupture odds ratios with increasing wGRS quartile for all three LMM, using the first wGRS quartile as a reference (FIGS. 4 and 5)

TABLE 4

Genetic risk scoring in anterior cruciate ligament rupture case and control Labrador Retriever dogs using GWAS associated SNPs from linear mixed model analysis

| LMM | Number of Risk alleles | | Significance |
| --- | --- | --- | --- |
| | Control | Case | |
| GCTA | 24 (16, 40) | 35 (24, 43) | P<2.2E−16 |
| GEMMA | 33 (22, 43) | 45 (29, 55) | P<2.2E−16 |
| PUMA | 62 (37, 84) | 77 (56, 99) | P<2.2E−16 |

Note:
Data represent median (range) for allele counting (cGRS). LMM Linear mixed models used were GCTA, GEMMA, PUMA. The Mann-Whitney U test was used to determine significance.

AUC differences between cGRS and wGRS were small and we found that there were no significant differences in ROC AUC for cGRS and wGRS for any of the three LMM analyses. For both cGRS and wGRS analyses, GCTA and GEMMA yielded increased ROC AUC values, when compared with PUMA. Overall, cGRS for GEMMA yielded the highest AUC at 0.9634 (Table 5).

TABLE 5

Receiver operating characteristic (ROC) analysis of genetic risk scoring in anterior cruciate ligament rupture case and control Labrador Retriever dogs using GWAS associated SNPs from linear mixed model analysis

| LMM | Area under the ROC curve | | Significance | |
| --- | --- | --- | --- | --- |
| | cGRS | 95% confidence interval | wGRS | 95% confidence interval |
| GCTA | 0.9487 | 0.9191-0.9725 | 0.9464 | 0.9183-0.9694 |
| GEMMA | 0.9634 | 0.9369-0.9824 | 0.9601 | 0.933-0.9801 |
| PUMA | 0.8842* | 0.8356-0.9158 | 0.8909* | 0.8458-0.9263 |

Note:
LMM Linear mixed models used were GCTA, GEMMA, PUMA. *Significantly different from GCTA and GEMMA (P < 0.005 for cGRS and P < 0.05 for wGRS).

GWAS Pathways are Enriched for Aggrecan Signaling:

Functional annotation clustering using DAVID revealed association with a cluster of four genes (CD209, ACAN, KLRA1, KLRD1) (P<2.3E−03, $P_{corr}$=0.059) that includes aggrecan (ACAN), a large structural protein that stabilizes the collagen network in ligament matrix. Using INRICH, we identified enrichment for a single set of genes (TTR, SLC9A5, SLC10A1, SLC37A4, SLC6A1, AQP9. GABRP, GJB1, KCNJ3, ALB, GABRB3, P2RX1, SLC16A2) (P<4.0E−4, $P_{corr}$=0.07). This pathway primarily consists of genes encoding membrane transport proteins with a wide range of physiological functions including pH regulation, glucose homeostasis, signal transduction.

ACL Rupture in the Labrador Retriever has Moderate Heritability:

Using a Bayesian method, narrow sense genetic heritability of ACL rupture was estimated at 0.538. Broad sense heritability from pedigrees was estimated at 0.521. After correction to the liability scale for a binary trait, these estimates were 0.493 and 0.476, respectively.

Discussion

By undertaking a within-breed GWAS in the Labrador Retriever, we found 98 regions of association with the trait, suggesting that ACL rupture is a complex, potentially highly polygenic condition. These loci explained between 48% and 56% of the disease risk phenotype, depending on which LMM was used for the association analysis, suggesting that inherited factors make an important contribution to the disease. We estimated narrow sense genetic heritability to be 0.49 and broad sense heritability to be 0.48, higher values than past estimates in the Newfoundland and Boxer breeds. Wilke V L, Conzemius M G, Kinghorn B P, Macrossan P E, Cai W, Rothschild M F. Inheritance of rupture of cranial cruciate ligament in Newfoundlands. J Am Vet Med Assoc. 2006; 228: 61-64. Nielen A L, Janss L L, Knol B W. Heritability estimations for diseases, coat color, body weight, and height in a birth cohort of Boxers. Am J Vet Res. 2001; 62: 1198-1206.

Our study population of Labrador Retriever dogs was typical of the general population, with an approximately equal numbers of male and female dogs and a large majority of the dogs being neutered by castration or ovariohysterectomy, respectively. ACL rupture in dogs is an acquired condition. In the present study, ACL rupture cases were middle-aged dogs typically, with a mean age of 6.0 years. In dogs, loss of sex steroids through neutering is a risk factor for ACL rupture (Whitehair J G, Vasseur P B, Willits N H. Epidemiology of cranial cruciate ligament rupture in dogs. J Am Vet Med Assoc. 1993; 203: 1016-1019). In human beings, ACL rupture is predisposed to female athletes (Sutton K M, Bullock J M. Anterior cruciate ligament rupture: Differences between males and females. J Am Acad Orthop Surg. 2013; 21: 41-50). Knee laxity in women is lowest in the follicular phase of the menstrual cycle (low estrogen), when ACL rupture is most common. Beynnon B D, Johnson R J, Braun S, Sargent M, Bernstein I M, et al. The relationship between menstrual cycle phase and anterior cruciate ligament injury. Am J Sports Med. 2006; 34: 757-764. Hewett T E, Zazulak B T, Myer G D. Effects of the menstrual cycle on anterior cruciate ligament injury risk. Am J Sports Med. 2007; 35: 659-668. This suggests that the influence of sex steroid levels on ACL laxity in both species may influence accumulation of matrix damage over time and consequently risk of rupture.

Because of the high LD within breeds of dogs, risk loci often contained large numbers of genes. However, several risk loci appeared to contain rSNPs located in gene deserts in intergenic regions of the genome of >500 kb that lack annotated genes or protein-coding sequences. Schierding W, Cutfield W S, O'Sullivan J M. The missing story behind genome wide association studies: single nucleotide polymorphisms in gene deserts have a story to tell. Front Genet. 2014; 5: 39. Complex trait disease is caused by disturbance to biological networks, not isolated genes or proteins. Regulatory SNPs can influence gene expression through a number of mechanisms that include the three dimensional organization of the genome, RNA splicing, transcription factor binding, DNA methylation, and long non-coding RNAs (lncRNA). Huang Q. Genetic study of complex diseases in the post-GWAS era. J Genet Genomics. 2015; 42: 87-98. Investigation of SNPs associated with complex trait disease in dogs with potential regulatory function through expressed quantitative trait loci (eQTL) studies or other methods is currently lacking.

One locus consisting of a 5 kb haplotype block with two other SNPs on CFA 24 met genome-wide significance in the present study. Ten genes were identified in this block with diverse physiological effects on cellular and tissue homeostasis. For example, ACTR5 plays an important role in chromatin remodeling during transcription, DNA repair, and DNA regulation. DHX35 encodes an ATP-ase that plays a role in RNA splicing and RALBAPB as well as FAM83D are both important for mitotic regulation. While a relationship between cellular homeostasis/proliferation and ACL rupture has not been established, it is feasible that aberrations in the genes that govern these processes could have a wide range of effects that may alter ligament tissue integrity. Other genes in this block include LBP and BPI, which have in important function regarding immuno-stimulatory capacity of innate immune mechanisms. Certain LBP genotypes have been associated with chronic inflammatory disease (Schumann R. Old and new findings on lipopolysaccharide-binding protein: a soluble pattern-recognition molecule. Biochem Soc Trans. 2011:39: 989-993). Notably, PPP1R16B encodes a protein that promotes angiogenesis through inhibition of Phosphatase and tensin homolog (PTEN) (Obeidat M, Li L, Ballermann B. TIMAP promotes angiogenesis by suppressing PTEN-mediated Akt inhibition in human glomerular endothelial cells. Am J Physiol Renal Physiol. 2014:307: F623-F633). The angiogenesis-associated signaling cascade is important for ligament matrix remodeling following mechanical loading, and variations in this cascade have been associated with non-contact ACL rupture risk (Rahim M, Gibbon A, Hobbs H, vander Merwe W, Posthumus M, Collins M, et al. The association of genes involved in the angiogenesis-associated signaling pathway with risk of anterior cruciate ligament rupture. J Orthop Res. 2014; 32: 1612-1618).

To further investigate the large number of genes we identified within risk loci, we also undertook pathway analysis of our data using two different methods. Pathway analysis using DAVID revealed an association with a cluster of four carbohydrate-binding protein genes including aggrecan (ACAN). Aggrecan is a large aggregating proteoglycan that, through binding to fixed charged groups, maintains osmotic pressure in collagenous tissues to promote water retention. Tissue hydration is important for efficient distribution of load and for the ability of cells to accomplish repair. Equine degenerative suspensory ligament desmitis (DSLD), a debilitating disorder of horses that leads to collagen disruption and eventual failure of the suspensory ligament, is associated with a 15-fold increase in aggrecan content of affected ligaments (Plaas A, Sandy J D, Liu H, Diaz M A, Schenkman D, Magnus R P, et al. Biochemical identification and immunolocalization of aggrecan, ADAMTS5 and inter-alpha-tryspin-inhibitor in equine degenerative suspensory ligament desmitis. J Orthop Res. 2011; 29: 900-906). Moreover, recent work has linked human ACAN rs1516797 with the risk of ACL injury in both male and female participants (Mannion S, Mtintsilana A, Posthumus M, van der Merwe W, Hobbs H, Collins M, et al. Genes encoding proteoglycans are associated with risk of anterior cruciate ligament ruptures. Br J Sports Med. 2014; 48: 1640-1646). A separate study revealed ACAN gene expression is up-regulated in ACL samples from female compared to male patients that have undergone ACL repair surgery, suggesting a possible etiology for the observed sex differences among patients with ACL injury. The precise mechanism by which ACAN up-regulation may lead to ligament weakening is currently unclear, though a structural change appears to be the most likely etiology.

We also tested genomic regions associated with ACL rupture for gene set enrichment using INRICH. One pathway, module 415 from the Molecular Signatures Database, was inflated. This pathway included 13 genes, most of which encode membrane transport proteins with various physiological roles. GJB1 is a member of the large connexin family and encodes connexin 32, a gap junction protein that has been implicated in the regulation of collagen synthesis and the matrix remodeling response to mechanical loading of tendon. Young N J, Becker D L, Fleck R A, Goodship A E, Patterson-Kane J C. Maturational alterations in gap junction expression and associated collagen synthesis in response to tendon function. Matrix Biol 2009; 28: 311-323. Waggett A D, Benjamin M, Ralphs J R. Connexin 32 and 43 gap junctions differentially modulate tenocyte response to cyclic mechanical load. Eur J Cell Biol. 2006; 85: 1145-1154. Other genes in this module are associated with central nervous system function. SLC6A1, GABRP, and GABRB3 are all associated with GABA signaling and mutations in TTR and have been associated with sensorimotor polyneuropathy. Previous work has suggested a role for neurological pathways in susceptibility to ACL rupture in Newfoundland dogs. Baird A E G, Carter S D, Innes J F, Ollier W, Short A. Genome-wide association study identifies genomic regions of association for cruciate ligament rupture in Newfoundland dogs. Animal Genetics. 2014; 45: 542-549.

ACL rupture GRSs were calculated for each dog to determine the cumulative effect of ACL rupture-associated loci on disease risk. While previous work found that wGRS better accounted for genetic risk (Chen H, Poon A, Yeung C, Helms C, Pons J, Bowcock A M, et al. A genetic risk score combining ten psoriasis risk loci improves disease prediction. PLoS One. 2011; 6: e19454), our study found no difference between cGRS and wGRS for any of the LMMs used. This is consistent with the idea that the ACL rupture phenotype is associated with a large number of genetic loci with small effects. In diseases with genetic loci with large effects, wGRS would more accurately represent the cumulative effect of individual loci on genetic risk. Overall, predictive capability of GRS is high, with a cGRS for GEMMA AUC of approximately 96%, indicating that we have clearly captured genetic loci that contribute to ACL rupture risk in our LMM association analysis. Future work should include verification of predictive capability by applying these methods to a new test cohort of case and control dogs.

Narrow and broad sense heritability of ACL rupture was estimated at 0.49 and 0.46 respectively using a Bayesian method. These estimates are considerably higher than restricted maximum likelihood (REML) heritability estimates that have been calculated for other breeds of dog. It is unclear whether ACL rupture is truly more heritable in the Labrador Retriever compared to other breeds or if the higher value is a reflection of the Bayesian method used. REML estimation of heritability was attempted but was not successful, probably because of the size of the data set.

Best Linear Unbiased Prediction:

A regression analysis was performed on the n=174 dog data set using GCTA-brand Software. The GCTA software is available online at http://www.complextraitgenomics.com/software/gcta/. See also Yang J, Lee S H, Goddard M E and Visscher P M. GCTA: a tool for Genome-wide Complex Trait Analysis. *Am J Hum Genet.* 2011 January 88(1): 76-82. (PubMed ID: 21167468). Specifically, a restricted maximum likelihood (REML) analysis of the genetic relationship matrix was executed, followed by a genomic best linear unbiased prediction (gBLUP) analysis to arrive at an estimate of total genetic effect (i.e., a breeding value) for each dog. This analysis was then converted to the SNP effects. The 22 SNPs most statistically associated with the phenotype are tabulated in Table 6. The gBLUP coefficients in Table 6 indicate that there are two SNPS that have much larger coefficients than the rest. There are six SNPS with much smaller coefficients, and 14 SNPS with a coefficient of intermediate size. (The positive or negative sign of the coefficients is not relevant; the coefficients are ranked according to their absolute magnitude.)

TABLE 6

BLUP Analysis Results

| snp | chr | ref allele | blup |
|---|---|---|---|
| BICF2S23135243 | 4 | A | 0.000633434 |
| BICF2G630371956 | 23 | A | 0.00058239 |
| BICF2P401973 | 10 | A | −0.000398919 |
| BICF2P526639 | 27 | G | 0.000373218 |
| BICF2S23448539 | 17 | A | −0.000367718 |
| BICF2G630114782 | 16 | A | −0.00036446 |
| BICF2P890246 | 9 | A | −0.000358272 |
| BICF2P170661 | 6 | A | 0.00034582 |
| BICF2G630815470 | 16 | G | −0.000335841 |
| BICF2G630815474 | 16 | A | −0.000335841 |
| TIGRP2P78405_rs9180048 | 6 | A | 0.000317864 |
| BICF2S2356299 | 27 | A | 0.000316762 |
| BICF2P1121006 | 18 | G | −0.000308138 |
| BICF2P260555 | 27 | A | 0.000275776 |
| BICF2P1465216 | 35 | A | 0.000272433 |
| BICF2P599385 | 35 | A | 0.000254262 |
| BICF2P154295 | 5 | C | 0.00021946 |
| BICF2S23645462 | 18 | A | 0.000202448 |
| BICF2P471347 | 27 | A | 0.000197961 |
| BICF2G630373050 | 23 | A | 0.000147584 |
| BICF2P1126668 | 4 | C | −0.000183486 |
| BICF2P412007 | 6 | A | 2.50967E−05 |

Bayesian and Machine Learning Models:

There are multiple methods for genomic prediction. Each method has advantages and disadvantages with respect to model assumptions and how well the model fits the data. With respect to prediction of complex traits, points to consider when choosing a model include the genetic architecture of the trait in terms of the potential presence of major genes, epistatic interactions, and a polygenic component. In addition, other factors to be considered include marker density and the strength of LD among them, as well as sample size. Bayesian models lend themselves well to genomic prediction, as they have the ability to incorporate prior information about expected SNP effects, for example allowing SNPs to have varying effect sizes, which makes more sense biologically than assuming all SNPs have the same effect size. Classification-based machine learning methods have also gained popularity for genomic prediction of binary traits. Here, a GWAS training set is viewed as a supervised classification problem whereby individuals are partitioned into case or control groups, and each group can be described using a combination of SNP inputs that may have one of 3 discrete values corresponding to the number of minor alleles present at each SNP. (See Botta, V., G. Louppe, P. Geurts, and L. Wehenkel, 2014 Exploiting SNP correlations within random forest for genome-wide association studies. PLoS One. 9: e93379.). Because no single model has been shown to perform best across data sets and traits (Pérez, P. and G. de Los Campos, 2014 Genome-wide regression and prediction with the BGLR statistical package. Genetics. 198: 483-495.), the following analyses were performed to investigate the feasibility of genomic prediction of ACL rupture in the dog model using several Bayesian and machine learning approaches. Provided here is insight on which methods appear to be most suitable for genomic prediction of a complex trait disease in dogs.

Materials and Methods:

Data Collection and Phenotyping:

Client-owned Labrador Retrievers were recruited from the University of Wisconsin-Madison Veterinary Care teaching hospital and through online advertising. All owners gave informed consent to participate in the study. When possible, a four-generation pedigree was obtained to confirm purebred status. Each dog was carefully phenotyped through orthopedic exam and lateral stifle radiographs. ACL rupture in affected dogs was verified during surgical treatment. Dogs classified as controls were over the age of 8 years, negative for palpable knee laxity, and showed no signs of joint effusion or osteophytosis that would be consistent with ACL rupture on lateral stifle radiographs. This age cutoff was chosen because Labrador Retrievers 8 years of age and older have approximately a 6% chance of developing ACL rupture. (Reif, U. and C. W. Probst, 2003 Comparison of tibial plateau angles in normal and cranial cruciate deficient stifles of Labrador retrievers. Vet. Surg. 32: 385-389.) DNA was isolated from saliva or blood samples obtained in accordance with the Guide for the Care and Use of Laboratory Animals with approval from the Institutional Animal Care and Use Committee of the School of Veterinary Medicine, University of Wisconsin-Madison. SNP genotyping was performed using the Illumina Canine HD BeadChip, which contains approximately 230,000 SNPs distributed evenly across the canine genome (CanFam3.1). The Wisconsin dataset contained 336 dogs (134 cases, 202 controls). This study also used public data from a recent study that used the same genotyping platform to increase sample size by 287 Labrador Retriever dogs. Hayward J. J., M. G. Castelhano, K. C. Oliveira, E. Corey, C. Balkman et al., 2016 Complex disease and phenotype mapping in the domestic dog. Nat. Comm. 7:10460. The final dataset included genotyping data and covariates on 622 Labrador Retriever dogs (247 cases, 375 controls).

SNP Genotyping Quality Control:

Genotype data were filtered with PLINK for quality control. All samples had a genotyping call rate >95%. SNPs were excluded if minor allele frequency (MAF) was less than or equal to 0.05, if genotyping rate was less than or equal to 95% or if there was deviation from Hardy-Weinberg proportions at P<1E−07.

Experimental Design:

Exploration of the performance of Bayesian and classification-based machine-learning methods for predicting ACL rupture in Labrador Retrievers was evaluated using a 10-fold cross validation framework. In 10-fold cross validation, data is randomly split into 10 partitions, which remained fixed for all methods. In each fold of the validation, one partition is used as the test data set and the other nine partitions are used as the training dataset. The partition scheme used was similar to that in Gianola, D., 2013 Priors in whole-genome regression: the Bayesian alphabet returns. Genetics. 194: 573-596 and Gonzlez-Camacho, J. M., G. de Los Campos, P. Pérez, D. Gianola, J. E. Cairns et al. 2012. Genome-enabled prediction of genetic values using radial basis function neural networks. Theor. Appl. Genet. 125: 759-771. This procedure is repeated 10 times so that each fold is predicted once, using the other 9 folds as training data. The advantage of multiple-fold cross validation is that it allows the training dataset to remain large without sacrificing a portion of the dataset for testing, which is very useful especially when the whole dataset is small.

Data was split into folds before implementing feature selection for the models. Care was taken to ensure that feature selection was performed only with consideration to the training set without knowledge of the test set for each fold. The predictions were aggregated from the 10 folds and averaged across the runs. Prediction performance was scored using area under the ROC curve (AUC). This process was repeated 5 times for each model evaluated. Models were compared using the average AUC and standard deviation.

Removal of Highly Correlated SNPs:

Linkage disequilibrium (LD) is extensive in purebred dog populations. In genomic prediction, SNPs that are in LD with the risk loci serve as surrogates in the model. In some genomic prediction applications, however, the strong LD among SNPs may lead to diminished importance of the true risk loci or tag SNPs in the model, as their effects may end up being partially captured by many SNPs. To mitigate this effect, SNPs with LD $r^2$ greater than 0.7 were pruned using PLINK with a window size of 50 SNPs and overlap of 5 SNPs until no pairs remained. LD pruning was performed using the complete dataset before the dataset was split into folds. All models were compared with and without removal of highly correlated SNPs.

Covariates:

Covariates used in the study were known risk factors for ACL rupture in dogs: weight, sex, and neuter status (castration and ovariohysterectomy in males and females, respectively). While age data was also available, it was not considered as a covariate because age was part of the criteria used for selection of dogs to participate in the study. When age is considered as part of the model, this variable provides information about case or control status and ultimately biases predictive accuracy. Covariates were incorporated as additional features in each classification method alongside SNPs. Covariates were also evaluated independently as predictors of ACL rupture using 10-fold cross validation using a logistic regression model. The R package 'stats' (R Core Team, 2013. R: A language and environment for statistical computing. R Foundation for Statistical Computing, Vienna, Austria.) was used for implementation of the logistic regression function.

Bayesian Analyses:

Genomic prediction models were fitted using five Bayesian logistic model specifications: Bayesian ridge regression, Bayesian LASSO regression, Bayes A, Bayes B, and Bayes Cπ (Gianola et al. 2013). For each sample the genotypic predictors were defined as $m_{ij}$ with i=1, . . . , n, and j=1, . . . , p for genotypic values and the response vector y={$y_i$} defined as two possible values including presence $y_i$=1 or absence $y_i$=0 of ACL rupture for the $i^{th}$ individual. A probit link function P($y_i$=1|μ, α)=Φ($\eta_i$) was used where, Φ is a standard normal cumulative distribution function (CDF) and $\eta_i$ is a linear predictor given by:

$$\eta_i = 1\mu + Xb + \sum_{j=1}^{p} m_{ij}\alpha_j + e$$

Above, μ is an intercept, X is an incidence matrix of the fixed effects in b (weight, sex, and neutered status), p is the number of markers fitted, $m_{ij}$ is the genotype of the $i^{th}$ individual at the $j^{th}$ SNP marker, and $\alpha_j$ is the $j^{th}$ marker effect, and e is a vector of residual effects. Following Albert and Chib (1993) and Lee et al. (2003), the probit link function was implemented using a latent normally distributed variable $l_i$=$\eta_i$+$\varepsilon_i$ and assumed that $$y_i = \begin{cases} 1 & \text{if } \eta_i > \gamma \\ 0 & \text{if } \eta_i \leq \gamma \end{cases}$$

where γ is a threshold parameter; $\varepsilon_i$ is an independent normal model residual with mean zero and with variance set equal to 1 as the parameter is not likelihood identified. Albert, J. H. and S. Chib, 1993 Bayesian analysis of binary and polychotomous response data. J. Am. Stat. Assoc. 88: 669-679. Lee, K. E., N. Sha, E. R. Dougherty, M. Vannucci, B. K. Mallick, 2003 Gene selection: a Bayesian variable selection approach. Bioinformatics. 19: 90-97.

To perform variable selection, a vector δ of p indicator variables is introduced:

$$\delta_j = \begin{cases} 1 & \text{if } \alpha_j \neq 0 \text{ variable } j \text{ selected} \\ 0 & \text{if } \alpha_j = 0 \text{ variable } j \text{ not selected} \end{cases}$$

A standard Bayesian linear model was used for whole genome prediction using binary data, as follows:

$$p(\theta_M|y,\omega_M) \propto p(y|\theta_M)p(\theta_M|\omega_M)$$

where p($\theta_M$|y, $\omega_M$) is the conditional posterior density of the genomic parameters ($\theta_M$); μ was assigned a flat prior density, and the marker effects (α) were assigned independent and identically distributed informative priors, depending on the model; am represents the genomic hyperparameters. The expression p(y|$\theta_M$)=$\Pi_1^n\{[\Phi(\eta_i)]^{y_i}[1-\Phi(\eta_i)]^{1-y_i}\}$ is the conditional distribution of the phenotype given the linear predictor, and p($\theta_M$|$\omega_M$)∝p($\alpha_j$|$\omega_M$)p($\sigma_e^2$) is the joint prior distribution of model unknowns, given the hyperparameters. The prior density of marker effects, p($\alpha_j$|$\omega_M$), defines the specification of the various Bayesian methods inducing shrinkage and variable selection (Bayes B and Bayes Cπ have a scaled-t and a Gaussian prior, respectively), or shrinkage only (Bayes A, BRR, and BL with scaled-t, Gaussian and Laplace priors, respectively). For more details, see de los Campos et al. (2013). Models were run using the BGLR statistical package (Perez et al. 2014) in R (www.R-project.org) for a total of 52,000 iterations with the first 6,000 iterations discarded. Each Bayesian model employs different prior assumptions for marker effects. See de los Campos, G., J. M. Hickey, R. Pong-Wong, H. D. Daetwyler, and M. P. Calus, 2013 Whole-genome regression and prediction methods applied to plant and animal breeding. Genetics. 193: 327-345; and Pérez, P. and G. de Los Campos, 2014 Genome-wide regression and prediction with the BGLR statistical package. Genetics. 198: 483-495. A brief description denoting the difference between the models follows.

Bayesian Ridge Regression:

In Bayesian Ridge Regression (BRR), an independent Gaussian prior with common variance is assigned to each regression coefficient. This scenario assumes that all markers have some effect and shrinkage is applied homogenously across the dataset.

Bayesian LASSO Regression:

Bayesian Least Absolute Shrinkage and Selection Operator (LASSO) regression uses a double-exponential or Laplace prior distribution for marker effects. See Park, T. and G. Casella, 2008. The Bayesian LASSO. J. Am. Stat.

Assoc. 103: 681-686. This places a higher mass at zero, meaning it induces a strong shrinkage toward zero. This is a logical application in a situation where most of the many thousands of SNP markers available are assumed to have little or no effect on the trait being tested.

Bayes A:

Bayes A uses a scaled-t prior distribution for marker effects. Similar to Bayesian LASSO, this places a higher mass at zero, inducing strong shrinkage toward zero. The scaled-t distribution places slightly less emphasis on shrinkage toward zero, allowing more flexibility for marker effects than Bayesian LASSO (de los Campos et al. 2013). See Meuwissen T., B. J. Hayes, and M. E. Goddard, 2001 Prediction of total genetic value using genome-wide dense marker maps. Genetics. 157: 1819-1829.

Bayes B:

Bayes B assumes that most of the genetic markers have zero effect, so that the distribution can be described as a mixture model where n is the probability that the SNP has no effect and $(1-\pi)$ is the probability that the SNP contributes to genetic variance (Meuwissen et al. 2001). To run Bayes B, we used default prior rules in BGLR to give a weakly informative prior: $\pi_0=0.5$ and $P_0=10$ (de los Campos et al. 2013). Non-null marker effects are assumed to have a scaled-t prior distribution, as in Bayes A. Therefore, the model is fairly stringent, assuming that relatively few markers have non-null effects.

Bayes Cπ:

Bayes Cπ is a mixture model similar to Bayes B, where a prior distribution is assumed for the proportion of null effect markers and non-null effect markers. In Bayes Cπ, non-null effect markers are assumed to have a Gaussian prior with a common variance. As with Bayes B, we used default prior rules to run Bayes Cπ: $\pi_0=0.5$ and $P_0=10$. See Habier, D., R. L. Fernando, K. Kizilkaya, and D. J. Garrick, 2011 Extension of the Bayesian alphabet for genomic selection. BMC Bioinformatics. 12: 186.

Machine Learning Analyses:

Snp Selection:

SNPs were selected for inclusion in the training set by one of two filter methods: 1) ranked P-values from a linear mixed model GWAS using the R package 'gaston' (Perdry et al. 2015), where smaller P-values were considered more likely to be associated with ACL rupture (Perdry, H. and C. Dandine-Roulland, 2015 Package R 'gaston', (version 1.5.5). URL https://cran.r-project.org/web/packages/gaston/index.html) or 2) ranked SNPs based on the mean difference in allele frequency between cases and controls. SNPs with the largest mean difference were considered to be the most likely associated with ACL rupture. The number of genetic variants believed to affect ACL rupture in dogs is unknown, though there are likely hundreds to thousands of non-null effect SNPs. Therefore, prediction performance of each model was assessed at several SNP inclusion thresholds from 5 to 15,000 SNPs. For each SNP inclusion threshold, the ranked SNPs were chosen using only training data after the test fold was removed from the dataset. This procedure was performed separately for each of the five 10-fold cross validation runs.

Classification Methods:

Four classification methods were considered. A brief description of each method follows:

Weighted Subspace Random Forest:

In Random Forest (RF), a collection ("forest") of separate tree-structured classifiers each cast a vote for the classification of an input and the majority vote of the trees is chosen as the correct classification. (Breiman, L., 2001. Random forests. Mach. Learn. 45: 5-32.) This method has the benefits of being fast and unlikely to over-fit to the dataset. Further, it is easily optimizable and provides variable importance estimates for further feature refinement. One shortcoming of random forest for high-dimensional data is the random selection of features which can fail to consistently select informative features. To address this issue, weighted subspace random forest (wRF) was used in the final validation of the methods. wRF weights each of the SNPs based on correlation of the SNP with the case or control class. It then calculates probability based on weights and uses it for variable selection. wRF was implemented using the R package 'wsrf'. See Zhao, H., G. J. Williams, and J. Z. Huang, 2017 WSRF: an R package for classification with scalable weighted subspace random forests. J. Stat. Softw. 77: 1-30. Models were built using at least 1000 trees and the square root of the total number of features at each tree split.

Gradient Boosted Trees:

Similar to RF, gradient boosted trees (GBT) uses an ensemble of tree-based classifiers for phenotype prediction. However, instead of creating decision trees independently of the other trees, trees are created conceptually in serial order, with each new tree attempting to minimize the mean squared error of the previous trees (Natekin, A. and A. Knoll, 2013 Gradient boosting machines, a tutorial. Front. Neurobot. 7: 21). Gradient boosting theoretically provides an advantage over random forest at the cost of greater computational complexity and the need to tune hyperparameters. The R package 'xgboost' was used for implementation of gradient boosted trees. Chen, T., T. He, M. Benesty, V. Khotilovich, and Y. Tang, 2015 Xgboost: extreme gradient boosting. R package version 0.4-2: 1-4. Tuning of the hyperparameters was performed using 5-fold cross validation grid search techniques. The cross-validation function from xgboost was used to determine the number of rounds to run the algorithm. The hyperparameters used were learning rate eta=0.05, minimum loss reduction gamma=0.3, maximum tree depth=10, subsample ratio of columns when constructing trees=0.8, subsample ratio of training instances=0.8 and evaluation metric of binary classification error rate with 1000 rounds of training.

Naïve Bayes:

One of the first machine learning methods used in bioinformatics, Naïve Bayes (NB) is a classification method based on Bayes' theorem. A training set is used to calculate frequencies of genotypes in case or control individuals, and this information is used to calculate the probability of an unknown individual's classification. NB is known for being simple and computationally efficient, but it is prone to miscalibration when features are high in number, as is the case with SNP datasets. Though it has been theoretically outclassed by ensemble machine learning methods, NB is still an excellent baseline for comparing classifiers. The R package 'e1071' was used for NB implementation. Meyer, D., E. Dimitriadou, K. Hornik, A. Weingessel, and F. Leisch, 2017 e1071: misc functions of the department of statistics, probability theory group (Formerly: E1071), TU Wien. R package version 1.6-8.

K-Nearest Neighbors:

K-nearest neighbors (KNN) is the most simplistic classifier, as it does not build a classifier using the training data. Instead, KNN compares the unknown input with classification of the k-nearest data points and uses the features of these neighbors to classify the unknown input. If multiple classifications are possible, a majority vote is applied (Acikel, C., Y. A. Son, C. Celik, and H. Gul, 2016 Evaluation of potential novel variations and their interactions related to bipolar disorders: analysis of genome-wide association study data. Neuropsychiatr. Dis. Treat. 12: 2997-3004.). However, KNN also struggles when the number of inputs is very large. Because this method does not depend on training and tuning, it serves as another baseline method for comparing other classifiers. The R package 'caret' was used for KNN implementation. Kuhn, M., 2008 Building predictive models in R using the caret package. J Stat. Soft. 28: 1-26. The models considered the five closest neighbors for purposes of classification decisions.

Ensemble Learning:

Ensemble learning methods were applied to determine whether better predictive performance could be obtained when multiple classifiers are considered in aggregate. Two methods of ensemble learning were used, 1) n-agreement and 2) supervisory learning.

When the four machine learning algorithms described above were used with two methods of feature selection, a total of 8 base-level models were considered. For our n-agreement ensemble approach, we defined an ensemble agreement threshold at each integer n between 1 and 8, rendering a positive prediction if and only if at least n of the 8 base models agree on a positive prediction. This n-agreement ensemble was applied on each fold within the cross validation workflow at each integer value of n between 1 and 8. Within each fold, the value of n was saved for the scenario with the maximum AUC. The value of n and the maximum AUC were averaged across the 10 folds and 10-fold cross validation was repeated five times.

In the supervisory machine learning approach, predictions from each of the 8 base-level learners were used as features in 1) logistic regression or 2) random forest models. The cross-validation workflow was extended for this method. In this framework, wRF, GBT, NB, and KNN models were trained using 10-fold cross-validation. Then, the aggregated predictions from these models were randomly re-ordered and re-partitioned into 10 new folds and employed as predictors in an additional 10-fold cross-validation experiment using logistic regression and random forest models. The concept of training a prediction model using predictions of lower-level models as its features is called "stacked" ensembling, and is a well-established procedure. Wolpert, D., 1992 Stacked Generalization. Neural Netw. 5: 241-259. This protocol was also repeated five times for each supervisory model.

Results:

The final dataset included 622 Labrador Retriever dogs (247 cases and 375 controls). Among cases, there were 14 intact females, 25 intact males, 111 ovariohysterectomized females, and 97 castrated males. Among controls, there were 59 intact females, 65 intact males, 130 ovariohysterectomized females, and 121 castrated males. After SNP data quality control, 126,678 SNPs remained. After removing highly correlated SNPs from the dataset, 76,767 SNPs remained.

Bayesian Analyses:

The prediction accuracy for the Bayesian models was nearly identical across the different types of Bayesian models in each scenario (data not shown). Including covariates in the model improved prediction accuracy. Removal of highly correlated SNPs did not appear to have an effect on overall prediction accuracy, though it did appear to decrease variability of the estimate when covariates were considered.

Machine Learning Analyses:

Results of 10-fold cross validation experiments for machine-learning models are summarized in Table 7. In general, models performed similarly regardless of the model chosen or methods used for feature selection. When LD pruning was not performed and covariates were not considered, the best performing model was GBT with 10,000 SNPs derived from GWAS analysis (AUC=0.590 (0.049)). Removal of highly correlated SNPs through LD pruning did not have a significant effect on classifier performance, though the same level of performance was achieved with fewer SNPs for some models. Including covariates as predictors accentuated the performance of the classifiers, both with and without LD pruning. When covariates were not considered, model performance improved slightly as ore SNPs were added to the model. Once covariates were included, however, model performance tended to decrease with increasing numbers of SNPs (data not shown). The best performing model overall was wRF with 5 SNPs chosen through mean difference (AUC 0.792 (0.027)).

TABLE 7

Highest performing machine learning models in 10-fold cross validation for prediction of ACL rupture in Labrador Retriever dogs

| Model | Feature Selection | No. SNPs | AUC (SD) |
|---|---|---|---|
| No SNPs removed for LD; Covariates not considered | | | |
| wRF | GWAS | 7500 | 0.584 (0.048) |
| | meanDiff | 7500 | 0.572 (0.059) |
| GBT | GWAS | 10000 | 0.590 (0.049) |
| | meanDiff | 7500 | 0.588 (0.059) |
| NB | GWAS | 7500 | 0.584 (0.025) |
| | meanDiff | 7500 | 0.584 (0.055) |
| KNN | GWAS | 10000 | 0.553 (0.045) |
| | meanDiff | 7500 | 0.564 (0.039) |
| Highly correlated SNPs removed; Covariates not considered | | | |
| wRF | GWAS | 15000 | 0.599 (0.050) |
| | meanDiff | 7500 | 0.598 (0.056) |
| GBT | GWAS | 7500 | 0.599 (0.039) |
| | meanDiff | 7500 | 0.597 (0.040) |
| NB | GWAS | 750 | 0.587 (0.054) |
| | meanDiff | 7500 | 0.576 (0.036) |
| KNN | GWAS | 12500 | 0.565 (0.052) |
| | meanDiff | 5 | 0.567 (0.045) |
| No SNPs removed for LD; Covariates added to model | | | |
| wRF | GWAS | 10 | 0.782 (0.035) |
| | meanDiff | 5 | 0.767 (0.034) |
| GBT | GWAS | 10 | 0.770 (0.050) |
| | meanDiff | 100 | 0.749 (0.037) |
| NB | GWAS | 5 | 0.688 (0.033) |
| | meanDiff | 5 | 0.674 (0.038) |
| KNN | GWAS | 7500 | 0.562 (0.034) |
| | meanDiff | 12500 | 0.557 (0.039) |
| Highly correlated SNPs removed; Covariates added to model | | | |
| wRF | GWAS | 5 | 0.778 (0.025) |
| | meanDiff | 5 | 0.792 (0.027) |
| GBT | GWAS | 10 | 0.757 (0.027) |
| | meanDiff | 5 | 0.777 (0.031) |
| NB | GWAS | 5 | 0.683 (0.031) |
| | meanDiff | 5 | 0.699 (0.040) |
| KNN | GWAS | 15000 | 0.569 (0.038) |
| | meanDiff | 7500 | 0.567 (0.044) | wRF = weighted random forest;
GBT = gradient boosted trees;
NB = Naive Bayes;
KNN = K nearest neighbors;
AUC = Area under the ROC curve Ensemble Learning:

Ensemble learning did not result in gains in performance when compared to base learners in 10-fold cross validation (Table 8). In all scenarios, supervisory learning using logistic regression outperformed random forest and n-agreement.

Overall, the best performing supervisory model was logistic regression when base models were trained on 100 SNPs (AUC=0.703 (0.08)).

TABLE 8

Highest performing ensemble models in 10-fold cross validation

| Ensemble | N (SD) | No. SNPs | AUC (SD) |
|---|---|---|---|
| *No SNPs removed for LD; Covariates not considered* | | | |
| nAgreement | 5.86 (1.31) | 12500 | 0.598 (0.04) |
| GLM | N/A | 7500 | 0.611 (0.07) |
| RF | N/A | 5 | 0.583 (0.09) |
| *Highly correlated SNPs removed; Covariates not considered* | | | |
| nAgreement | 5.68 (1.17) | 4000 | 0.607 (0.04) |
| GLM | N/A | 4000 | 0.611 (0.06) |
| RF | N/A | 5 | 0.579 (0.09) |
| *No SNPs removed for LD; Covariates added to model* | | | |
| nAgreement | 5.14 (0.76) | 5 | 0.687 (0.07) |
| GLM | N/A | 25 | 0.695 (0.09) |
| RF | N/A | 5 | 0.692 (0.09) |
| *Highly correlated SNPs removed; Covariates added to model* | | | |
| nAgreement | 5.24 (0.96) | 10 | 0.694 (0.07) |
| GLM | N/A | 100 | 0.703 (0.08) |
| RF | N/A | 5 | 0.702 (0.09) |

N = average number of models that agreed on the prediction;
AUG = area under the ROC curve;
GLM = supervisory learning with logistic regression;
RF = random forest.

Covariate Analysis:

10-fold cross validation using a logistic regression model of sex, neuter status, and body weight reached an AUC=0.734 (0.032).

The Most Predictive SNPs for Canine Cruciate Ligament Rupture:

Using the above models, the SNPs found to be most predictive of canine cruciate ligament rupture are as listed in Table 9:

For all models except KNN, the best predictions were achieved when covariates were considered in the analysis. This is reasonable, as the heritability of ACL rupture in dogs has been estimated between 0.3 and 0.5. Baker L. A., B. Kirkpatrick, G. J. M. Rosa, D. Gianola, B. Valente et al., 2017 Genome-wide association analysis in dogs implicates 99 loci as risk variants for anterior cruciate ligament rupture. PLoS One. 12:e0173810. This means a substantial proportion of variance for ACL rupture is explained through environmental effects. When the genomic profile is considered alone, the maximum AUC that can be achieved in a classifying algorithm is dependent upon heritability of the trait and disease prevalence. As the disease prevalence of ACL rupture in the Labrador Retriever is 0.0579 (Witsberger, T. H., J. A. Villamil, L. G. Schultz, A. W. Hahn, and J. L. Cook, 2008 Prevalence of and risk factors for hip dysplasia and cranial cruciate ligament deficiency in dogs. J. Am. Vet. Med. Assoc. 232: 1818-1824), the maximum achievable AUC in a model that explains 100% of genetic variance, assuming a heritability of 0.4, is 0.861. (Wray, N. R., J. Yang, M. E. Goddard, and P. M. Visscher 2010 The genetic interpretation of area under the ROC curve in genomic profiling. PLoS Genet. 6: e1000864.) Given the relatively small sample size, the density of the SNP dataset, and prior evidence supporting the hypothesis that ACL rupture is highly polygenic (Baker et al. 2017), it is unlikely that we can explain 100% of genetic variance. The AUC achieved using SNP data alone is thus reasonable given the heritability and prevalence of ACL rupture in the Labrador Retriever population. Notably, the maximum AUC that can be achieved with a genomic profile that explains one quarter of genetic variance is 0.69, which is closer to the estimates achieved in this analysis.

The genomic prediction was performed using five Bayesian regression models that differed principally in the prior chosen for the effect distribution of the SNPs. In this study, the prediction performance across these five Bayesian models was roughly equivalent. Predictive performance across

TABLE 9

Most Predictive SNPs for Canine Cruciate Ligament Rupture

| No. | Chromosome | Position | SNP id | A1 | A2 | freqA2 | score | p-value |
|---|---|---|---|---|---|---|---|---|
| 1 | 18 | 32376379 | BICF2P1154648 | A | G | 0.8102894 | 19.23446 | 1.16E−05 |
| 2 | 3 | 83396156 | BICF2P479234 | G | A | 0.585209 | 18.54063 | 1.66E−05 |
| 3 | 18 | 32193170 | BICF2P819217 | A | G | 0.6189711 | 17.25798 | 3.26E−05 |
| 4 | 16 | 29105886 | BICF2G630111439 | G | A | 0.9766881 | 16.74404 | 4.28E−05 |
| 5 | 24 | 10526247 | BICF2S22934135 | A | G | 0.8151125 | 16.34414 | 5.28E−05 |
| 6 | 20 | 27044236 | BICF2P954610 | C | A | 0.6495177 | 16.297 | 5.41E−05 |
| 7 | 26 | 35663964 | BICF2P735764 | A | G | 0.5032206 | 16.05038 | 6.17E−05 |
| 8 | 33 | 11235061 | BICF2S23334334 | A | T | 0.7170418 | 15.90284 | 6.67E−05 |
| 9 | 9 | 28951974 | BICF2G630833451 | A | G | 0.8432476 | 15.84276 | 6.88E−05 |
| 10 | 9 | 50090278 | BICF2P890246 | A | C | 0.7845659 | 15.33646 | 9.00E−05 |
| 11 | 13 | 23873894 | BICF2G630616424 | A | G | 0.7950161 | 14.5049 | 1.40E−04 |
| 12 | 9 | 50094619 | BICF2P139678 | G | A | 0.7905844 | 14.36873 | 1.50E−04 |
| 13 | 35 | 13837803 | BICF2S22960034 | A | G | 0.7572581 | 14.19154 | 1.65E−04 |
| 14 | 23 | 19766375 | TIGRP2P302341_rs9124258 | A | G | 0.562341 | 13.98491 | 1.84E−04 |
| 15 | 18 | 32175945 | BICF2P528692 | A | G | 0.6374598 | 13.94777 | 1.88E−04 |
| 16 | 24 | 27275160 | BICF2G630500363 | A | G | 0.6985531 | 13.91962 | 1.91E−04 |
| 17 | 1 | 115007981 | BICF2S23119518 | A | C | 0.9750804 | 13.82616 | 2.01E−04 |
| 18 | 3 | 82363452 | BICF2P1379990 | G | C | 0.5442122 | 13.81134 | 2.02E−04 |
| 19 | 34 | 21313689 | BICF2P503821 | A | G | 0.9340836 | 13.76797 | 2.07E−04 |
| 20 | 1 | 16255217 | BICF2G630713129 | A | G | 0.7741158 | 13.73077 | 2.11E−04 |

The models disclosed herein demonstrate that it is feasible to predict ACL rupture using SNP data and relevant covariates from dogs given with a sufficiently large sample size.

models tends to be similar as long as they are tuned appropriately (Gianola et al. 2013). It should also be noted that there is a mismatch between the prior assumptions used by these models and the genetic architecture of ACL rupture. ACL rupture is expected to be highly polygenic (Baker et al. 2017) and none of the priors used for the Bayesian models tested in this study model a polygenic architecture, where many SNPs are expected to have some effect, most with a very small effect size. Therefore, it is logical that no Bayesian model stood out in comparison to the others, as no model has the advantage of a prior that matched expected distribution of SNP effects.

Prediction performance of the machine learning models was similar to the Bayesian models, with the best-performing classifiers slightly out-performing Bayesian regression. When covariates were not considered, all models performed similarly. All models except for KNN showed increased performance when covariates were included as features in the model, and in these scenarios, peak prediction performance was achieved with 5-10 SNPs. Of the classifiers, GBT and wRF tended to out-perform the simpler classifiers. Both NB and KNN struggle when the number of inputs is large, so their weakness here is perhaps unsurprising. Overall, the best performing model was GBT, and its performance remained fairly consistent as more SNPs were included as model features.

When covariates were considered independently, the average AUC achieved was only slightly lower than the top-performing classifiers. This indicates that the majority of the accuracy of prediction is relying on the inclusion of covariate risk factors for ACL rupture, though a small number of SNPs may be providing data that are sufficiently informative to improve prediction. It should be noted that dog weight is itself a complex trait that is partly genetically determined, so the covariates included in this study may also be capturing genetic effects at some level. Two of the ACL rupture risk factors that were included in this study are modifiable variables (dog weight and whether a dog was neutered). Ideally, a genomic prediction algorithm would identify high-risk dogs without these variables, so that clinical action could be taken to reduce risk. For example, the link between neutering and ACL rupture may only refer to dogs who are neutered before one year of age, which is common clinical practice. Neutering could then be delayed for dogs at high risk of ACL rupture. Age of neutering was not recorded for the present data. A similar approach could apply to counseling owners on the importance of maintaining a healthy adult weight. This is an important consideration for future models, which should try to capture as much genetic variance as possible so the model will rely less on covariates for predictive accuracy.

The machine learning approach implemented feature selection based solely on univariate filtering methods. In most cases, there was little to no difference in model performance between feature selection performed by GWAS or mean difference. When genotypic data is considered alone, some cases showed similar model performance with a smaller number of SNPs when mean difference was used for feature selection. By definition, mean difference chooses SNPs where there is a larger difference between cases and controls. So it is logical that ranking SNPs in this way may be advantageous when choosing SNPs for case-control classification.

Adding an additional decision-making layer through an ensemble learning approach did not lead to an appreciable gain in prediction performance, and often performed worse than some individual base models. Because ensembles often provide a performance improvement when inputs are uncorrelated, we suspect that correlation among base model outputs was high enough to prevent ensembles from having any benefit. We chose a stacked ensemble approach to perform supervisory machine learning models, as we were interested to learn whether a combination of the base level learners we used might improve prediction performance. We considered another common method for ensemble learning, where the data is partitioned and the testing set is used to calibrate the ensemble, evaluating accuracy in the left-out testing set. This method also did not lead to a gain in prediction performance.

The results, though, clearly demonstrate that genomic prediction of ACL rupture risk in dogs can be achieved with clinically relevant accuracy.

Biologically Enhanced Genome-Wide Association Study: Data Collection and Phenotyping:

All procedures were performed in accordance with the recommendations in the Guide for the Care and Use of Laboratory Animals of the National Institutes of Health and the American Veterinary Medical Association and with approval from the Animal Care Committee of the University of Wisconsin-Madison (protocols V1070, V5463), as described above. Dogs were genotyped using the Illumina Canine HD BeadChip (220,000 SNPs) and imputed to the higher density Axiom Canine HD array (710,000 SNPs) using Beagle 5.0 (B L Browning, Y Zhou, and S R Browning (2018). A one-penny imputed genome from next generation reference panels. Am J Hum Genet 103(3):338-348) and a multibreed reference panel containing 646 dogs of 35 breeds using a method outlined previously (Friedenberg S. G., Meurs K. M. (2016). Genotype imputation in the domestic dog. Mamm. Genome. 27, 485-494). Quality control was performed using PLINK 2 (Chang et al., 2015, supra). SNPs were removed from the dataset if they had minor allele frequency (MAF)<0.01, genotyping call rate <90%, or did not conform to Hardy-Weinberg proportions at a P-value less than 1E−07. Because BayesRC does not tolerate missing genotypes, SNPs with any missing genotypes were also removed from the dataset.

RNA Sequencing and Differential Gene Expression Analysis:

Anterior cruciate ligament and knee synovial tissue biopsies were collected from four ACL rupture affected cases and four unaffected control dogs. It was important to examine both ACL and synovium, as synovitis is known to precede ACL rupture in the dog and may play a role in disease progression and development of osteoarthritis. Cases and controls were matched as closely as possible based on breed, sex, neutered status, age, and weight (data not shown). Medications that the dogs were taking at the time of sample collection were also considered. Tissues from cases were collected during knee stabilization surgery. Tissues from unaffected control dogs were collected from dogs undergoing pelvic limb amputation or euthanasia for reasons unrelated to this study. Library preparation and sequencing was performed at the University of Wisconsin-Madison Biotechnology Center (Madison, Wisconsin). Illumina TruSeq RNA libraries were constructed and 150 bp paired-end sequencing was performed using the Illumina Hi-Seq 2500 platform. Read quality was evaluated using FastQC (Andrews S. (2010). FastQC: a quality control tool for high throughput sequence data. Available online at: www.bioinformatics.babraham.ac.uk/projects/fastqc). Bioinformatic analysis of RNASeq reads adhered to ENCODE guidelines and best practices for RNA-Seq (ENCODE Consortium. ENCODE guidelines and best practices for RNA-Seq: Revised December 2016. ENCODE project. 2016. Available from: www.encodeproject.org/documents/cede0cbe-d324-4ce7-ace4-f0c3eddf5972/@@download/attachment/

ENCODE%20Best%20Practices%20for%20RNA_v2.pdf). Briefly, alignment of adapter-trimmed (Skewer v0.1.123) (Jiang H., Lei R., Ding S. W., Zhu S. (2014). Skewer: a fast and accurate adapter trimmer for next-generation sequencing paired-end reads. BMC Bioinformatics. 15:182. doi: 10.1186/1471-2105-15-182), 2×150 bp paired-end strand-specific Illumina reads to the canFam3.1 genome (assembly accession: GCA_000002285.2) was achieved with the Spliced Transcripts Alignment to a Reference (STAR v2.5.3a) software (Dobin A., Davis C. A., Schlesinger F., Drenkow J., Zaleski C., Jha S., Batut P., Chaisson M., Gingeras T. R. (2013). STAR: ultrafast universal RNA-seq aligner. Bioinformatics. 29, 15-21), and a splice-junction aware aligner using Ensembl annotation (Aken et al. (June 2016) The Ensembl gene annotation system, baw093. doi: 10.1093/database/baw093). Expression estimation was conducted using RSEM v.3.0 (RNASeq by Expectation Maximization) (Li B., Dewey C. N. RSEM: accurate transcript quantification from RNA-Seq data with or without a reference genome. BMC Bioinformatics. 2011; 12(1):323). To test for differential expression among individual group contrasts, expected read counts were used as input into edgeR v3.16.5 (Robinson M. D., McCarthy D. J., Smyth G. K. (2010). EdgeR: a Bioconductor package for differential expression analysis of digital gene expression data. Bioinformatics. 26, 139-140). Significance of the negative-binomial test was adjusted with a Benjamini-Hochberg FDR correction at the 5% level (Reiner A., Yekutieli D., Benjamini Y. (2003). Identifying differentially expressed genes using false discovery rate controlling procedures. Bioinformatics. 19, 368-375). Prior to statistical analysis with edgeR, independent filtering was performed, requiring a threshold of least 2 reads per million in at least 3 samples. The validity of the Benjamini-Hochberg FDR multiple testing procedure was evaluated by inspection of the uncorrected p-value distribution. Lists of differentially expressed genes were submitted for pathway analysis using PANTHER classification system (Mi H., Muruganujan A., Casagrande J., Thomas P. D. (2013). Large-scale gene function analysis with the PANTHER classification system. Nat. Protoc. 8, 1551-1566) to analyze for statistical overrepresentation using the Fisher's Exact test. Significance was defined as P<0.05 after correction for false discovery rate (FDR).

Association Analysis and Assignment of Biological Priors:

BayesRC is an extension of the Bayesian mixture model BayesR described above. The BayesR algorithm assumes that SNP effects are derived from a mixture of four normal distributions including a zero-effect distribution. The three effect distributions are $N(0, 0.0001\sigma^2_g)$, $N(0, 0.001\sigma^2_g)$, and $N(0, 0.01\sigma^2_g)$, with 62 g representing the additive genetic variance explained by the SNPs. This mixture of distributions approximates the various SNP effect sizes that typically describe the underlying genetic architecture of complex traits. A mostly uninformative Dirichlet prior ($\alpha=(1,1,1,1)$) was used to define the prior proportion of SNPs in each distribution. The BayesRC algorithm was run for a total of 200,000 iterations with a burn-in period of 100,000 iterations. The model was repeated five times to assess model convergence. See Moser G., Lee S. H., Hayes B. J., Goddard M. E., Wray N. R., Visscher P. M. (2015). Simultaneous discovery, estimation and prediction analysis of complex traits using a Bayesian mixture model. PLoS Genet. 11, e1004969. doi: 10.1371/journal.pgen.1004969 and MacLeod I. M., Bowman P. J., Vander Jagt C. J., Haile-Mariam M., Kemper K. E., Chamberlain A. J., Schrooten C., Hayes B. J., Goddard M. E. (2016). Exploiting biological priors and sequence variants enhances QTL discovery and genomic prediction of complex traits. BMC Genomics. 17, 144. doi: 10.1186/s12864-016-2443-6

SNPs were assigned to biological prior classes if they were within or near a candidate gene defined through RNA sequencing or reported in peer-reviewed literature (data not shown). SNPs were assigned to classes if they were within the boundaries of a gene±25 kb. The size of the flanking region was conservatively defined by calculating the average haplotype block size in our data using PLINK, which was 19.43 kb with a maximum haplotype block size of 200 kb. Gene boundaries were based on canFam3.1 from Ensembl release 97 using the python package PyEnsembl v1.7.5. Because some Labrador Retrievers in the current dataset were present in the datasets of our previously published work (Baker et al., 2017; Baker et al., 2018, supra), candidate genes identified through associations from our previous studies were not included in the candidate gene class to avoid introducing bias. Though we had defined ACAN as a candidate gene in our previous work (Baker et al., 2017), we chose to include ACAN in the candidate gene class because our previously reported association was weak. All other SNPs were assigned to a separate class. Fixed effects included in the analysis were dog sex, age, weight, and neutered status as well as the top five principal components derived from eigen decomposition of the variance-standardized genetic relationship matrix. Principal components analysis was performed using PLINK. Final mean SNP effects were evaluated based on the absolute value of the reported SNP effect. SNP effects were assigned to genes if they were within the gene boundary+/−25 Kb.

Selection Signature Analysis:

ACL rupture in dogs has a marked breed predisposition, with reported breed prevalence in the Labrador Retriever of 5.79% (Witsberger et al., 2008). It is possible that ACL rupture risk was inadvertently selected during artificial selection for desirable breed traits. Our goal for selection signature analysis was to detect regions that show preferential selection in the genomes of case versus control subpopulations. To accomplish this, we performed whole genome scans for signatures of selection based on the concept of extended haplotype homozygosity (EHH). See Sabeti P. C., Reich D. E., Higgins J. M., Levine H. Z., Richter D. J., Schaffner S. F., Gabriel S. B., Platko J. V., Patterson N. J., McDonald G. J., Ackerman H. C. (2002). Detecting recent positive selection in the human genome from haplotype structure. Nature. 419, 832-837. In EHH analysis, reduction in haplotype diversity is computed as the probability that two extended haplotypes around a given locus are the same, given that they have the same allele at the locus.

We defined haplotypes for case and control subpopulations using fastPHASE software with the number of random starts set to 10 (–T10) and the number of iterations set to 20 (–C20). See Scheet P., Stephens M. (2006). A fast and flexible statistical model for large-scale population genotype data: applications to inferring missing genotypes and haplotypic phase. Am. J. Hum. Genet. 78, 629-644. The fastPHASE model is based on the idea that, over short regions of the genome, haplotypes in a population tend to cluster into groups of similar haplotypes. The number of clusters, K, is an essential hyperparameter that must be computed. To define K, a portion of the data is set to missing, and for several values of K, fastPHASE makes a best guess for the missing genotypes. This process is repeated multiple times, each time choosing a different portion of the observed data to set to missing. The chosen value for K is the one that produced the lowest overall error rate. We assigned the upper limit for the number of clusters equal to 40 (−Ku40) and the lower limit to 10 (−K110), with an interval of 5 (−Ki5). The masking procedure was repeated 100 times (−Ks100), randomly selecting 500 SNP loci (−Ks500) and 5% of observed genotypes among individuals (−Kp0.05) to be masked.

To define selection signatures, we calculated the cross-population extended haplotype heterozygosity test (XP-EHH) using the R package "rehh" (M. Gautier and R. Vitalis (March 2012) Bioinformatics 28(8):1176-7). XP-EHH compares the integrated EHH between two populations at the same SNP. Selection signatures are identified based on overrepresented haplotypes in one population compared to the other (Sabeti et al., 2007). We evaluated case and control populations to assess whether selection pressures have affected individuals in the case category relative to the founder population (unaffected control dogs). See Voight B. F., Kudaravalli S., Wen X., Pritchard J. K. A map of recent positive selection in the human genome. PLoS Biol. 4, e72. doi: 10.1371/journal.pbio.0040072. Candidate SNPs were defined using a threshold of $-\log_{10}(P \leq 1E-05)$. Genome-wide significance was defined at $-\log_{10}(P \leq 1E-08)$.

Results:

BayesRC: A Hierarchical Bayesian Mixture Model that Incorporates Prior Biological Knowledge:

We used the BayesRC algorithm (MacLeod et al., 2016, supra) to perform a genome-wide association analysis that incorporated prior biological knowledge, which we defined through RNA sequencing of disease-relevant tissues and peer-reviewed literature. To assign biological priors, each SNP variant in the dataset was assigned a priori to a specific class where each class represented a category of biological information. Separately for each class, a Markov Chain Monte Carlo (MCMC) approach was used to estimate SNP effects from an independent mixture of four normal distributions of varying SNP effect sizes including a zero-effect distribution. As the algorithm runs, it uses genotype data to estimate the probability that each SNP belongs within each effect size distribution and updates the proportions with each iteration. Updating the distribution of SNP effects separately for each class is an advantage if any one class is enriched for associated loci. A uniform prior is applied across all classes to ensure that biological information only influences the analysis if the data supports it (MacLeod et al., 2016).

Labrador Retriever Dataset for Genome-Wide Association:

The dataset included 397 (156 ACL rupture affected and 241 unaffected control) purebred Labrador Retriever dogs. Of these, 55 were intact males, 30 were intact females, 161 were castrated males, and 151 were ovariohysterectomized females. After quality control 443,227 SNPs remained for analysis.

Defining Biological Priors for GWAS:

To define genes with relevance to ACL rupture in the dog model, we performed RNA sequencing (RNA-Seq) on ACL and knee synovium that was collected from four ACL rupture cases and four matched control dogs. FastQC analysis determined that all samples were of good quality. Overall, average coverage and mapping were excellent across samples. There were 98,214,398 average reads per sample. The average primary and secondary alignment percentages were 90.18% and 8.21% respectively. The average proportion of properly paired reads was 99.97%. After adjustment for multiple testing and without imposing a threshold for log fold change, we identified 200 genes from ACL tissue and 444 genes from synovium tissue that were significantly differentially expressed between case and control dogs (data not shown). To ease interpretation of results, only transcript ID's that could be matched to a known gene were included in the assignment of biological priors. This left a total of 181 differentially expressed genes (DEGs) from ACL and 373 DEGs from synovium for prior assignment.

To evaluate the biological relevance of DEGs identified in each tissue, gene lists were submitted to the PANTHER classification system (Mi et al., 2013) for pathway analysis. PANTHER analysis did not identify overrepresented pathways among DEGs identified in ligament. There were two overrepresented pathways among DEGs from case and control synovium (Table 10).

TABLE 10

Overrepresented pathways identified from differentially expressed genes (DEGs) derived from synovium tissue collected from ACL rupture cases and matched controls

| PANTHER Pathway | Number observed | Number expected | FDR P-value |
|---|---|---|---|
| B lymphocyte activation | 8 | 1.41 | 8.17E−03 |
| T lymphocyte activation | 9 | 1.64 | 5.91E−03 |

Pathway overrepresentation was calculated using Fisher's Exact test in PANTHER version 15.0 (Mi et al., 2013). FDR = False discovery rate.

We defined three biological prior classes for BayesRC based on differential gene expression analysis: DEGs in ACL, DEGs in knee synovium, and DEGs identified in both tissues. A fourth class represented candidate genes that have been reported to be associated with ACL rupture or tendinopathy in human or dog studies. SNPs were assigned to classes based on proximity to candidate genes. SNPs that were not within or near candidate genes were assigned to a separate class. Ultimately, 12,209 SNPs were assigned to biological priors (Table 11).

TABLE 11

The number of SNPs assigned to biological priors defined by differential gene expression analysis and candidate genes reported in the literature

| Class | Definition | Number of SNPs |
|---|---|---|
| ACL | Differentially expressed genes in ACL | 2,614 |
| SYN | Differentially expressed genes in knee synovium | 7,850 |
| A&S | Differentially expressed genes in ACL and knee synovium | 703 |
| CAND | Candidate genes | 1,042 |
| NA | SNPs not assigned to biological priors | 431,018 |

SNP = single nucleotide polymorphism

Association Analysis:

SNP effects were averaged over five runs. Overall, an average of 3,728 SNPs (0.8%) had some estimated effect, with the remainder of SNPs assigned to the zero-effect distribution. GWAS results are visually represented in a Manhattan plot (FIG. 1). On average, 37 SNPs were assigned to the $0.01\sigma^2$ g distribution, 361 SNPs were assigned to the $0.001\sigma^2$ g distribution, and 3,330 SNPs were assigned to the $0.0001\sigma^2$ g distribution. The 50 largest SNP effects and their distance to genes are reported in Table 12.

TABLE 12

The 50 largest SNP effects from Bayesian mixture model (BayesRC) association analysis that included biological priors

| Chromosome: Location | Class | SNP Effect | Gene | Distance (bp) |
|---|---|---|---|---|
| chr9:53865770 | ACL | 0.006 | FNBP1 | 9,144 |
| chr9:53871457 | ACL | 0.005 | FNBP1 | 3,457 |
| chr7:49455960 | NA | −0.004 | None | 0 |
| chr5:64359450 | ACL | 0.004 | ACSF3 | 21,679 |
| chr24:34970050 | NA | 0.004 | None | 0 |
| chr3:51975977 | CAND | −0.003 | ACAN | 19,131 |
| chr24:34842049 | NA | −0.003 | SULF2 | 0 |
| chr24:38868995 | NA | −0.003 | Noncoding transcript | 467 |
| chr5:64356666 | ACL | 0.002 | ACSF3 | 19,554 |
| chr10:16199198 | NA | 0.002 | None | N/A |
| chr10:20536317 | A&S | −0.002 | FBLN1 | 0 |
| chr35:23442178 | SYN | 0.002 | LRRC16A | 0 |
| chr25:33171736 | SYN | −0.002 | ADAM28 | 23,934 |
| chr10:16138674 | NA | 0.002 | ENSCAFG00000031351 | 19,408 |
| chr13:47443664 | CAND | −0.002 | KDR | 0 |
| chr11:12024840 | CAND | 0.002 | LOX | 0 |
| chr32:28999310 | A&S | 0.002 | RPL34 | 4,462 |
| chr32:28996275 | A&S | 0.002 | RPL34 | 0 |
| chr12:32821658 | CAND | −0.002 | COL9A1 | 0 |
| chr7:49422990 | NA | −0.002 | None | N/A |
| chr15:2674794 | A&S | 0.002 | ZMPSTE24 | 0 |
| chr24:32151336 | CAND | 0.002 | WISP2 | 0 |
| chr12:32792729 | CAND | −0.002 | COL9A1 | 0 |
| chr9:43053330 | ACL | −0.002 | FLOT2 | 0 |
| chr1:57856871 | A&S | −0.002 | NEPN | 0 |
| chr15:31879223 | CAND | −0.002 | DCN | 0 |
| chr3:59287831 | CAND | −0.002 | SORCS2 | 0 |
| chr1:41687833 | A&S | 0.002 | AKAP12 | 0 |
| chr7:49415778 | NA | −0.002 | None | N/A |
| chr10:16118097 | NA | 0.002 | None | N/A |
| chr12:32815853 | CAND | −0.002 | COL9A1 | 0 |
| chr24:32144138 | CAND | −0.002 | WISP2 | 0 |
| chr7:49426351 | NA | −0.001 | None | N/A |
| chr1:31289631 | A&S | −0.001 | ABRACL | 22,185 |
| chr5:9055237 | A&S | −0.001 | PKNOX2 | 0 |
| chr9:60820860 | A&S | −0.001 | DAB2IP | 0 |
| chr9:9241561 | CAND | 0.001 | ITGB3 | 17,351 |
| chr6:47617815 | CAND | −0.001 | COL11A1 | 0 |
| chr12:2604649 | CAND | −0.001 | HLA-DPB1 | |
| chr36:30472199 | CAND | 0.001 | COL3A1 | 16,392 |
| chr3:59282629 | CAND | −0.001 | SORCS2 | 0 |
| chr12:36850837 | CAND | −0.001 | COL12A1 | 12,221 |
| chr6:47604275 | CAND | −0.001 | COL11A1 | 0 |
| chr17:34324882 | A&S | −0.001 | ARID5A | 0 |
| chr23:34306524 | NA | −0.001 | DZIP1L | 0 |
| chr12:36852892 | CAND | −0.001 | COL12A1 | 14,276 |
| chr12:36767540 | CAND | −0.001 | COL12A1 | 0 |
| chr17:26672332 | ACL | 0.001 | FAM98A | 0 |
| chr15:2655972 | A&S | 0.001 | COL9A2 | 0 |
| chr3:52046039 | CAND | −0.001 | HAPLN3 | 0 |

SNP = single nucleotide polymorphism. Class refers to the biological prior the SNP was assigned to with ACL-Differentially expressed genes in ACL; SYN-Differentially expressed genes in knee synovium; A&S-Differentially expressed genes in ACL and knee synovium; CAND-Candidate genes; NA-SNPs not assigned to biological priors. SNPs with a distance of 0 are located within the listed gene.

Selection Signature Analysis:

Artificial selection is a necessary part of breed creation, and genetic risk of ACL rupture in the Labrador Retriever may have be the result of unintentional selection due to linkage between ACL rupture risk variants and desirable traits. Regions of the genome that have been under selection have reduced heterozygosity which is identifiable through selection signature analysis. ACL rupture risk variants that are also within regions of the genome that are under selection may be especially important to defining breed predisposition to ACL rupture. To define selection signatures, we calculated the cross population extended haplotype homozygosity (XP-EHH) test between case and control populations. Overall, 11 regions of the genome contained genomic regions that showed high levels of differentiation between case and control populations (Table 13). Significant selection signatures were identified on chromosomes 4, 5, 9, and 27. The selection signatures on chromosomes 9 and 5 are 11.9 Mb and 5.5 Mb from two regions among the 10 largest SNP effects. The positive XP-EHH value on both of these regions indicate that they are under positive selection.

TABLE 13

SNPs from selection signature analysis using the XP-EHH test between ACL rupture case and control populations with $P \leq 1E\text{-}05$

| Chromsome: Location (bp) | XP-EHH statistic | $-\log_{10}$(P-value) |
|---|---|---|
| chr9:41939206 | 8.755 | 17.689 |
| chr4:12205862 | −6.752 | 10.835 |
| chr5:58850078 | 6.291 | 9.501 |
| chr27:26574198 | −5.938 | 8.541 |
| chr25:34033213 | 5.107 | 6.485 |
| chr33:7205917 | −4.595 | 5.363 |
| chr32:25969031 | −4.579 | 5.331 |
| chr26:3270682 | 4.539 | 5.248 |
| chr29:30730571 | −4.473 | 5.112 |
| chr7:44727369 | −4.467 | 5.101 |
| chr17:8919370 | 4.454 | 5.075 |

Positive XP-EHH values indicate regions that are under positive selection.
Negative XP-EHH values indicate regions that are under negative selection.

As shown by the above results, incorporation of prior biological information using the Bayesian mixture model algorithm BayesRC provides a more objective approach to prioritize SNPs based on biological probability of effect in GWAS analysis. This is a contrast to the subjective decisions that are often made when evaluating GWAS results (Thompson et al., 2013). Here, we were able to identify associations within or near many relevant candidate genes for ACL rupture. Many of the largest effect SNPs were within or near genes that were either differentially expressed between ACL rupture case and control dogs.

Kits:

Kits are provided which contain reagents useful for determining the presence or absence of polymorphisms appearing in the loci and/or genes recited in Table 1. The kits are used with the methods described herein to determine a dog's propensity to develop CCLR.

The kits typically include written instructions. The instructions may optionally provide calibration curves or charts for comparison with the experimentally measured values. The kit generally includes oligonucleotide probes and/or primers that bind specifically with the canine loci identified in Table 1 and thus function to reveal the presence (or absence) of the corresponding SNP. An appropriate amount of the oligonucleotide primers is provided in one or more containers. The primers may also be provided in the form of a "gene chip" or addressed array, such as (for example) those described in U.S. Pat. No. 7,510,841. In such an array, the primers or probes are immobilized on a solid substrate, typically in pre-determined, known locations. The oligonucleotide primers may also be provided suspended in an aqueous solution or as a freeze-dried or lyophilized powder. The container(s) in which the oligonucleotide(s) are supplied can be any conventional container that is capable of holding the supplied form, for instance, hermetically sealed pouches, microfuge tubes, ampoules, or bottles. In some applications, pairs of primers may be provided in pre-measured single use amounts in individual, typically disposable, tubes or equivalent containers. With such an arrangement, the sample to be tested for the presence of SNPs can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction.

In some embodiments, kits may optionally also include the reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of SNPs. In certain embodiments, these probes will be specific for a potential polymorphic site that may be present in the target amplified sequences. The appropriate sequences for such a probe will be any sequence that includes one or more of the identified polymorphic sites, particularly those nucleotide positions indicated in Table 1, such that the sequence the probe is complementary to is a polymorphic site. As a general rule, the probes are at least 6 nucleotides in length and typically shorter than roughly 50 nucleotides. The polymorphic site may occur at any position within the length of the probe. It is often beneficial to use longer probes, in order to ensure specificity. Thus, in some embodiments, the probe is at least 8, at least 10, at least 12, at least 15, at least 20, or at least 30 nucleotides.

It may also be advantageous to provide in the kit one or more control sequences for use in the amplification reactions. The design of appropriate positive control sequences is well known to one of ordinary skill in the appropriate art. By way of example, control sequences may comprise canine nucleic acid molecule(s) with known sequence at or near one or more of the target SNP positions described in Table 1.

The kits may optionally include either labeled or unlabeled oligonucleotide probes for use in detection of the in vitro amplified target sequences. The appropriate sequences for such a probe will be any sequence that falls between the annealing sites of the provided oligonucleotide primers, such that the sequence to which the probe is complementary is amplified during the PCR reaction. In certain embodiments, these probes will be specific for a potential polymorphism that may be present in the target amplified sequences.

It may also be advantageous to provide in the kit one or more control sequences for use in the PCR reactions. The design of appropriate positive control sequences is well known to one of ordinary skill in the appropriate art.

Additional components in specific kits may include instructions for carrying out the assay described herein.

CONCLUSIONS

Candidate loci are identified herein which are associated in a statistically significant manner with heritable non-contact CCLR in the Labrador retriever. The regions identified in this study are useful to guide breeding decisions.

What is claimed is:

1. A method for breeding a dog, the method comprising:
a) isolating genomic DNA from a first dog;
b) assaying the genomic DNA of step (a) for one or more single nucleotide polymorphisms (SNPs) selected from the group consisting of:

| SNP | Dog chromosome location |
|---|---|
| BICF2P1154648 | 18 |
| BICF2P479234 | 3 |
| BICF2P819217 | 18 |
| BICF2G630111439 | 16 |
| BICF2S22934135 | 24 |
| BICF2P954610 | 20 |
| BICF2P735764 | 26 |
| BICF2S23334334 | 33 |
| BICF2G630833451 | 9 |
| BICF2G630616424 | 13 |
| BICF2S22960034 | 35 |
| TIGRP2P302341_rs9124258 | 23 |
| BICF2P528692 | 18 |
| BICF2S23119518 | 1 |
| BICF2P1379990 | 3 |
| BICF2P503821 | 34, and |
| BICF2G630713129 | 1 | c) detecting an allele that is not associated with non-contact cranial cruciate ligament rupture at one or more of the SNPs recited in step (b) in the genomic DNA of step (b);
d) selecting a first dog having an allele from step (c) that is not associated with non-contact cranial cruciate ligament rupture; and then
e) breeding the first dog having at least one allele that is not associated with non-contact cranial cruciate ligament rupture at one or more of the SNPs recited in step (b) in the genomic DNA of step (b).

2. The method of claim 1, wherein step (b) comprises assaying the genomic DNA for five or more single nucleotide polymorphisms (SNPs).

3. The method of claim 1, wherein step (b) comprises assaying the genomic DNA for ten or more single nucleotide polymorphisms (SNPs).

4. The method of claim 1, wherein step (b) comprises assaying the genomic DNA for fifteen or more single nucleotide polymorphisms (SNPs).

5. The method of claim 1, wherein step (b) comprises assaying the genomic DNA for SNPs at all of:

| SNP | Dog chromosome location |
| --- | --- |
| BICF2P1154648 | 18 |
| BICF2P479234 | 3 |
| BICF2P819217 | 18 |
| BICF2G630111439 | 16 |
| BICF2S22934135 | 24 |
| BICF2P954610 | 20 |
| BICF2P735764 | 26 |
| BICF2S23334334 | 33 |
| BICF2G630833451 | 9 |
| BICF2G630616424 | 13 |
| BICF2S22960034 | 35 |
| TIGRP2P302341_rs9124258 | 23 |
| BICF2P528692 | 18 |
| BICF2S23119518 | 1 |
| BICF2P1379990 | 3 |
| BICF2P503821 | 34, and |
| BICF2G630713129 | 1 | step (c) comprises detecting an allele that is not associated with non-contact cranial cruciate ligament rupture any of the SNPs recited in step (b) in the genomic DNA of step (b); and step (e) comprises breeding the first dog having alleles that are not associated with non-contact cranial cruciate ligament rupture at all of the SNPs recited in step (b) in the genomic DNA of step (b).

6. The method of claim 1, further comprising a) isolating genomic DNA from a second dog;

b) assaying the genomic DNA from the second dog for one or more single nucleotide polymorphisms (SNPs) selected from the group consisting of:

| SNP | Dog chromosome location |
| --- | --- |
| BICF2P1154648 | 18 |
| BICF2P479234 | 3 |
| BICF2P819217 | 18 |
| BICF2G630111439 | 16 |
| BICF2S22934135 | 24 |
| BICF2P954610 | 20 |
| BICF2P735764 | 26 |
| BICF2S23334334 | 33 |
| BICF2G630833451 | 9 |
| BICF2G630616424 | 13 |
| BICF2S22960034 | 35 |
| TIGRP2P302341_rs9124258 | 23 |
| BICF2P528692 | 18 |
| BICF2S23119518 | 1 |
| BICF2P1379990 | 3 |
| BICF2P503821 | 34, and |
| BICF2G630713129 | 1 | c) detecting an allele that is not associated with non-contact cranial cruciate ligament rupture at one or more of the SNPs recited in step (b) in the genomic DNA of step (b); and d) selecting a second dog having an allele from step (c) that is not associated with non-contact cranial cruciate ligament rupture; and then e) breeding the second dog with the first dog when the second dog has at least one allele that is not associated with non-contact cranial cruciate ligament rupture at one or more of the SNPs recited in step (b) in the genomic DNA of step (b).

7. The method of claim 6, wherein step (b) comprises assaying the genomic DNA of the second dog for five or more single nucleotide polymorphisms (SNPs).

8. The method of claim 6, wherein step (b) comprises assaying the genomic DNA of the second dog for ten or more single nucleotide polymorphisms (SNPs).

9. The method of claim 6, wherein step (b) comprises assaying the genomic DNA of the second dog for fifteen or more single nucleotide polymorphisms (SNPs).

10. The method of claim 6, wherein step (b) comprises assaying the genomic DNA from the second dog for SNPs at all of:

| SNP | Dog chromosome location |
| --- | --- |
| BICF2P1154648 | 18 |
| BICF2P479234 | 3 |
| BICF2P819217 | 18 |
| BICF2G630111439 | 16 |
| BICF2S22934135 | 24 |
| BICF2P954610 | 20 |
| BICF2P735764 | 26 |
| BICF2S23334334 | 33 |
| BICF2G630833451 | 9 |
| BICF2G630616424 | 13 |
| BICF2S22960034 | 35 |
| TIGRP2P302341_rs9124258 | 23 |
| BICF2P528692 | 18 |
| BICF2S23119518 | 1 |
| BICF2P1379990 | 3 |
| BICF2P503821 | 34, and |
| BICF2G630713129 | 1 | step (c) comprises detecting at least one allele that is not associated with non-contact cranial cruciate ligament rupture in any of the SNPs recited in step (b) in the genomic DNA of step (b); and step (e) comprises breeding the first dog with the second dog when the second dog has alleles that are not associated with non-contact cranial cruciate ligament rupture at all of the SNPs recited in step (b) in the genomic DNA of step (b).

* * * * *